(12) United States Patent
Kurihashi

(10) Patent No.: US 6,383,192 B1
(45) Date of Patent: May 7, 2002

(54) APPARATUS FOR INTUBATION OF LACRIMAL DUCT

(75) Inventor: Katsuaki Kurihashi, Hamamatsu (JP)

(73) Assignee: MLC Limited Company (JP)

( * ) Notice: Subject to any disclaimer, the term of this patent is extended or adjusted under 35 U.S.C. 154(b) by 0 days.

(21) Appl. No.: 09/553,771

(22) Filed: Apr. 21, 2000

(30) Foreign Application Priority Data

| Apr. 28, 1999 | (JP) | 11-122927 |
| Jun. 17, 1999 | (JP) | 11-170456 |
| Aug. 11, 1999 | (JP) | 11-227554 |
| Aug. 26, 1999 | (JP) | 11-239706 |

(51) Int. Cl.[7] .................................................. A61F 11/00
(52) U.S. Cl. .................. 606/108; 606/107; 606/198; 604/8; 604/294
(58) Field of Search ................ 606/108, 107, 606/191, 198, 199; 604/8, 9, 10, 285, 294, 28, 175

(56) References Cited

U.S. PATENT DOCUMENTS 4,658,816 A * 4/1987 Ector, Jr. ...................... 604/8
5,437,625 A * 8/1995 Kurihashi ...................... 604/8
6,117,116 A * 9/2000 Walsh ......................... 604/264
6,238,363 B1 * 5/2001 Kurihashi ...................... 604/8
6,238,364 B1 * 5/2001 Becker .......................... 604/8

* cited by examiner

Primary Examiner—Pedro Philogene
(74) Attorney, Agent, or Firm—Lorusso & Loud

(57) ABSTRACT

An apparatus for intubation of the lacrimal duct comprising a thinner tube (or rod), a thicker tube(s) extending from one end or both ends of a thinner tube (or rod) and a probe which is inserted through a small cut applied to the thicker tube(s) wherein for the tube to be pushed into the lacrimal duct using a probe, the inner surface of the thicker tube(s) has a step(s), protuberance(s), groove(s) and septum (septa), and the shape of the inner space of the thicker tube is the frustum of a circular cone, and for the probe to be removed easily, lubricants such as olive oil, lipiodol ultrafluid, ointment and so on are applied to the surface of the probe and/or inner part of the thicker tube, and also the thinner tube (or rod) is longer than the canalicular length for the boundary portion (s) between the thinner tube (or rod) and thicker tube(s) to be positioned in the lacrimal sac—nasolacrimal duct to get better stability in the lacrimal duct.

17 Claims, 31 Drawing Sheets

APPARATUS FOR INTUBATION OF LACRIMAL DUCT

TECHNICAL BACKGROUND

This invention relates to an apparatus for intubation of lacrimal duct (lacrimal drainage pathway) for treatment of lacrimal duct obstruction and so on.

PRIOR ART

A typical prior method of silicone intubation is shown in Japanese Patent Publication No. 56-50579.

In the prior method, the silicone tube is drawn into the lacrimal duct by a probe which is pulled out from the inferior nasal meatus.

Therefore, in the previous methods, a probe as a guide must be pulled out from the nostril. This maneuver is difficult. It is not rare that it takes a lot of time to retrieve the probes from the nostril or the retrieval is impossible.

For many years the present inventor has studied keenly for the treatment of lacrimal duct obstruction and dry eye, apparatus for intubation of the lacrimal duct which can be used easily with decreased pain to patients, can be quickly and correctly inserted into the lacrimal duct, is not easily dislocated during the intubation period, and can be easily removed after accomplishment of treatment.

As a result, various kinds of apparatus for intubation have been invented, for example, as shown in Japanese Patent Publication No. 2811283, Japanese Patent Publication No. 2572340, Japanese Patent Publication No. 2539325, Japanese Patent Publication No. 8-19271, Japanese Patent Publication No. 8-30104, Japanese Patent Publication No. 9-276318, Japanese Patent Publication No. 2572352, Japanese Patent Publication No. 10-256109.

Above all, the apparatus shown in Japanese Patent Publication No. 2539325 is a typical invention made by the present inventor.

As shown in FIGS. 1~3, in the typical prior art apparatus, the central part 20~40 mm of the tube 50~120 mm in length is thinner and softer, and the bilateral parts of the tube are thicker, and both ends are sharp pointed and closed. Thus, the apparatus for intubation of the lacrimal duct resembling a "nunchaku" type device which is used by Chinese martial art practitioners, has been developed.

FIG. 3 (A) shows a cross sectional view showing a conventional nunchaku-style tubing.

As shown in FIG. 3, the thicker tube 42 is pushed into the lacrimal duct with the probe 61 which is inserted into the thicker tube. At the time, if there is too much lubricity between the probe 61 and the thicker tube 42, the tube sometimes cannot be inserted into the lacrimal duct because the tip of the probe 61 slips on the inner surface X of the thicker tube, whereas, if the lubricity between the probe 61 and the thicker tube 42 is poor, the thicker tube sometimes turns back in the lacrimal duct together with the probe 61 when the probe 61 is removed from the thicker tube 42 (see for example, Kurihashi K: Dacryology, Medical A01 Shuppan, Inc, 1998, p.171).

SUMMARY OF THE INVENTION

One object of the present invention is to provide an apparatus which can be easily pushed into the lacrimal duct with the tip of a probe by making the inner surface of the thicker tube uneven.

Another object of the present invention is to provide an apparatus in which the probe can be easily removed from the thicker tube by making better lubricity between the probe and the thicker tube.

According to one mode of the invention, a step(s), protuberance(s), groove(s), other irregular surface and/or septum (septa) is applied to the inner surface of the thicker tube to make the inner surface uneven, and a septum (septa) is also applied.

By doing so, the thicker tube can be easily pushed into the lacrimal duct because the tip of the probe touches the step(s), protuberance(s), groove(s), other irregular surface or septum (septa). Furthermore lubricants such as olive oil, lipiodol ultrafluid and/or ointment are applied to the inner part of the thicker tube and/or probe. By doing so, better lubricity is provided between the thicker tube and the surface of the probe.

Although the columnar shape is good for the shape of the inner surface of the thicker tube, the frustum of the circular cone is better for the shape of the inner surface to operate the apparatus for intubation of the lacrimal duct. The shape of the frustum of the circular cone makes the thicker tube able to be pushed more effectively into the lacrimal duct.

The materials and shapes for the thicker tube and probe described in Japanese Patent Publication No. 2811283, Japanese Patent Publication No. 2572340, Japanese Patent Publication No. 2539325, Japanese Patent Publication No. 2572352, Japanese Patent Publication No. 8-19271, Japanese Patent Publication No. 8-30104, Japanese Patent Publication No. 9-276318, Japanese Patent Publication No. 10-256109 can be used for the present invention.

DETAILED DESCRIPTION OF THE EMBODIMENTS

Embodiment shown in FIGS. 4~20

Figure 1:
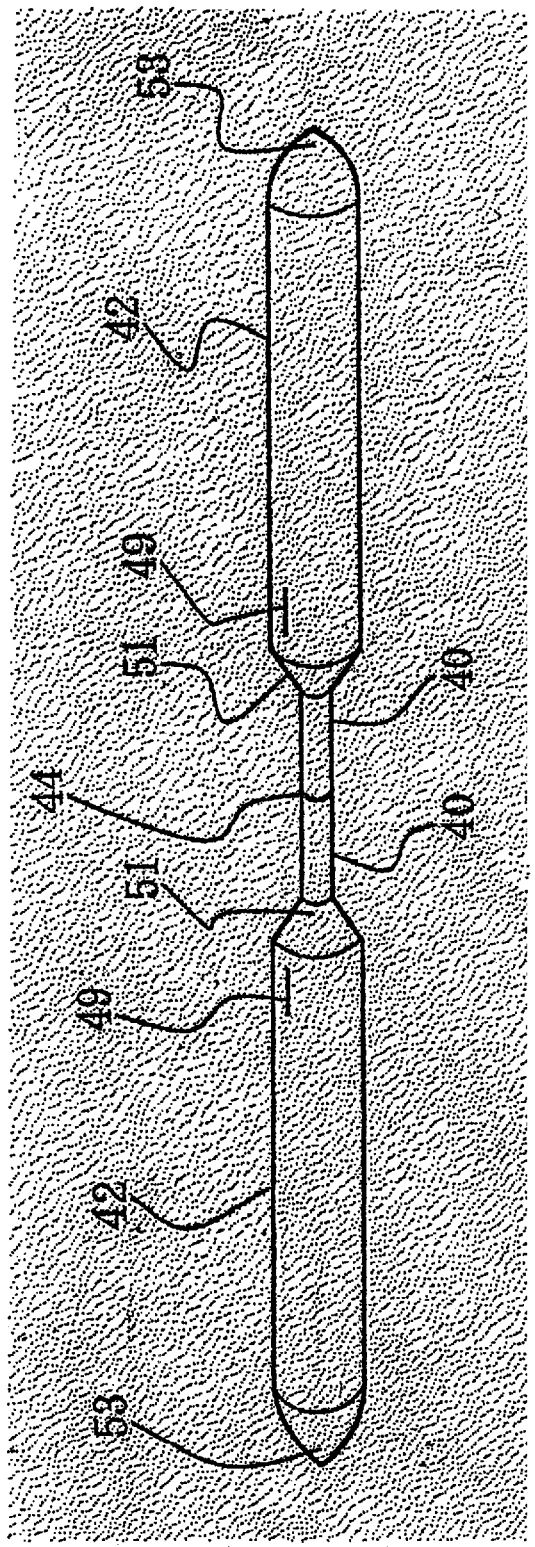
FIG. 1 is a perspective view showing a conventional nunchaku-style tube.

As shown in FIG. 4(A), thicker tubes are connected with both ends of the thinner tube (or rod), while the inner surface of the thicker tube has steps g1, g2, g3 and the tip of the thicker tube 42 is sharp pointed, conical in shape and closed.

As shown in FIG. 4(A) (B), lubricant 55 such as olive oil, lipiodol ultrafluid, and/or ointment is applied to the inner part of the thicker tube and/or probe in advance.

Small cuts (1.5~1.0 mm in length) 49 for the probe (0.25~0.4 mm in diameter) 61 to insert, are made. The small cuts 49 are applied to the thicker tubes parallel to the axis of the tube 42. The positions of the small cuts 49 are near the other end of the thicker tube 42. Markings corresponding to the positions of the small cuts make it easier to discover the small cuts.

The length and thickness of the tube depend on the length of the lacrimal duct and size of the inner space of the individual lacrimal ducts. The present invention (85~105 mm in total length) which consists of the central thinner tube (or rod) 40 (0.5 mm in thickness and 25 mm in length), and bilateral thicker tube 42, (1 mm in outer diameter, 0.5 mm in inner diameter and 30~40 mm in length) is most frequently used.

Although in order for the tube to be stable in the lacrimal duct, it is important that the central segment of the tube is thinner and softer, other optional shapes of it are also useful.

The middle point 44 of the central thinner segment is marked.

The thicker tubes 42 are connected with both ends of the thinner tube (or rod) with silicone adhesive.

Figure 4:
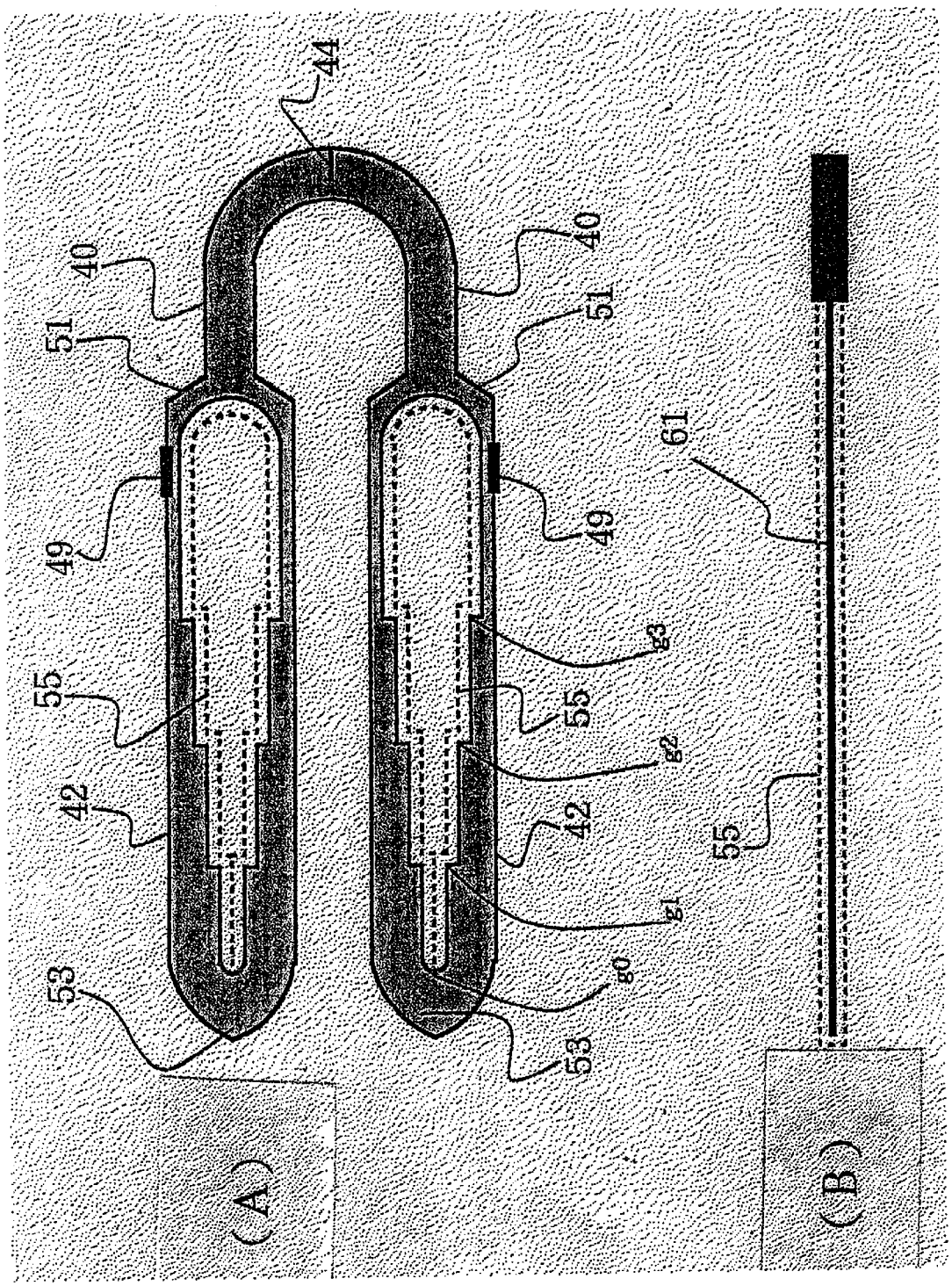
FIG. 4A is a sectional view showing lubricant(s) applied to an apparatus according to the present invention.
FIG. 4B is an explanatory diagram showing lubricant(s) applied to a probe according to the present invention.

As shown in FIG. 4, it is better to make a slope at the junction 51 between the thicker tube 42 and the thinner tube (a rod) 40.

As shown in FIG. 4, if the tip 53 of the thicker tube 42 is sharp pointed and in conical shapes, it is more easily inserted from the lacrimal puncta.

Figure 5:
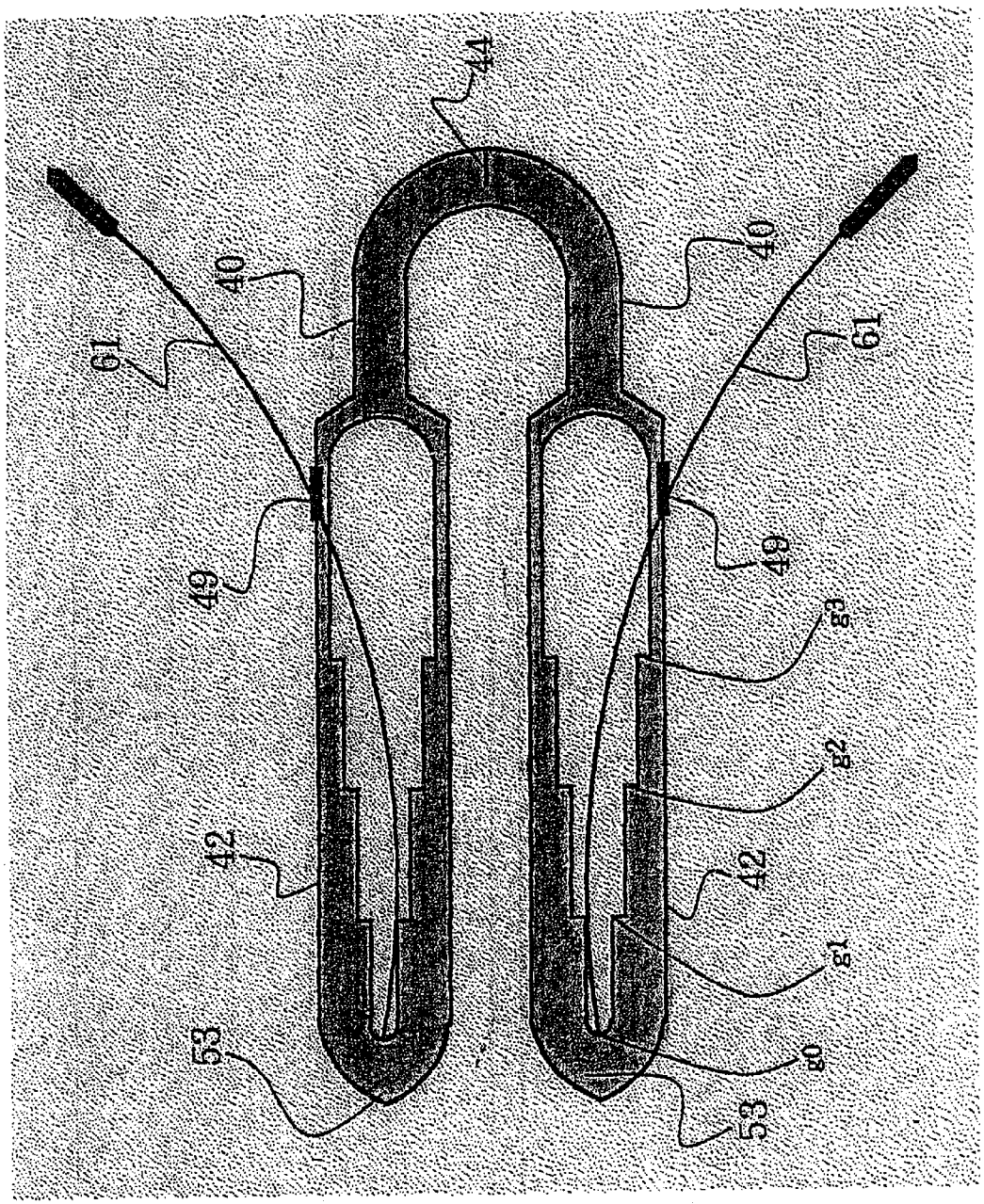
FIG. 5 is a sectional view showing an apparatus for intubation according to the present invention.

As shown in FIG. 5, the thicker tubes 42 equipped with probes 61 in advance are more convenient.

Figure 6:
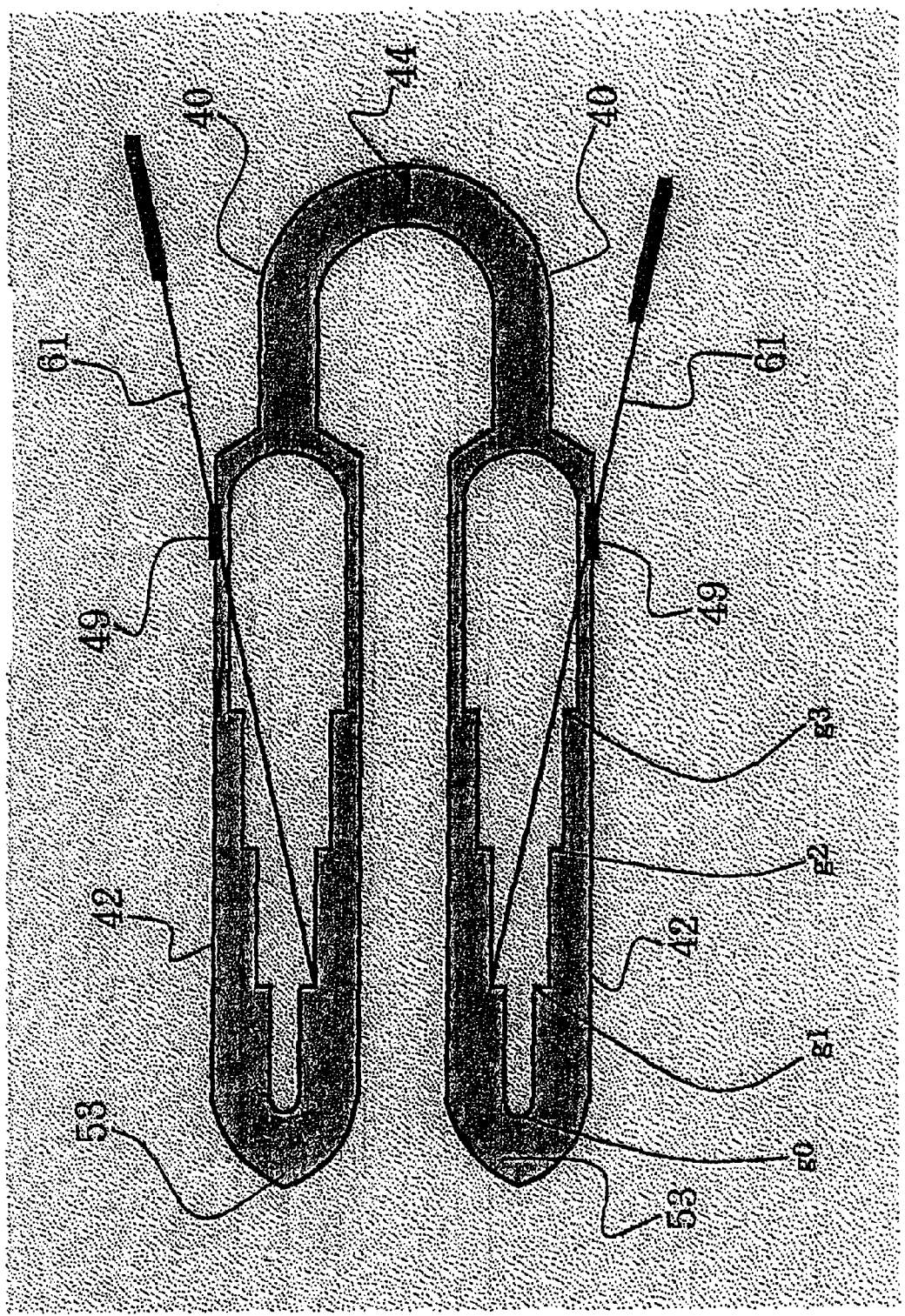
FIG. 6 is a sectional view showing an apparatus for intubation according to the present invention.
Figure 7:
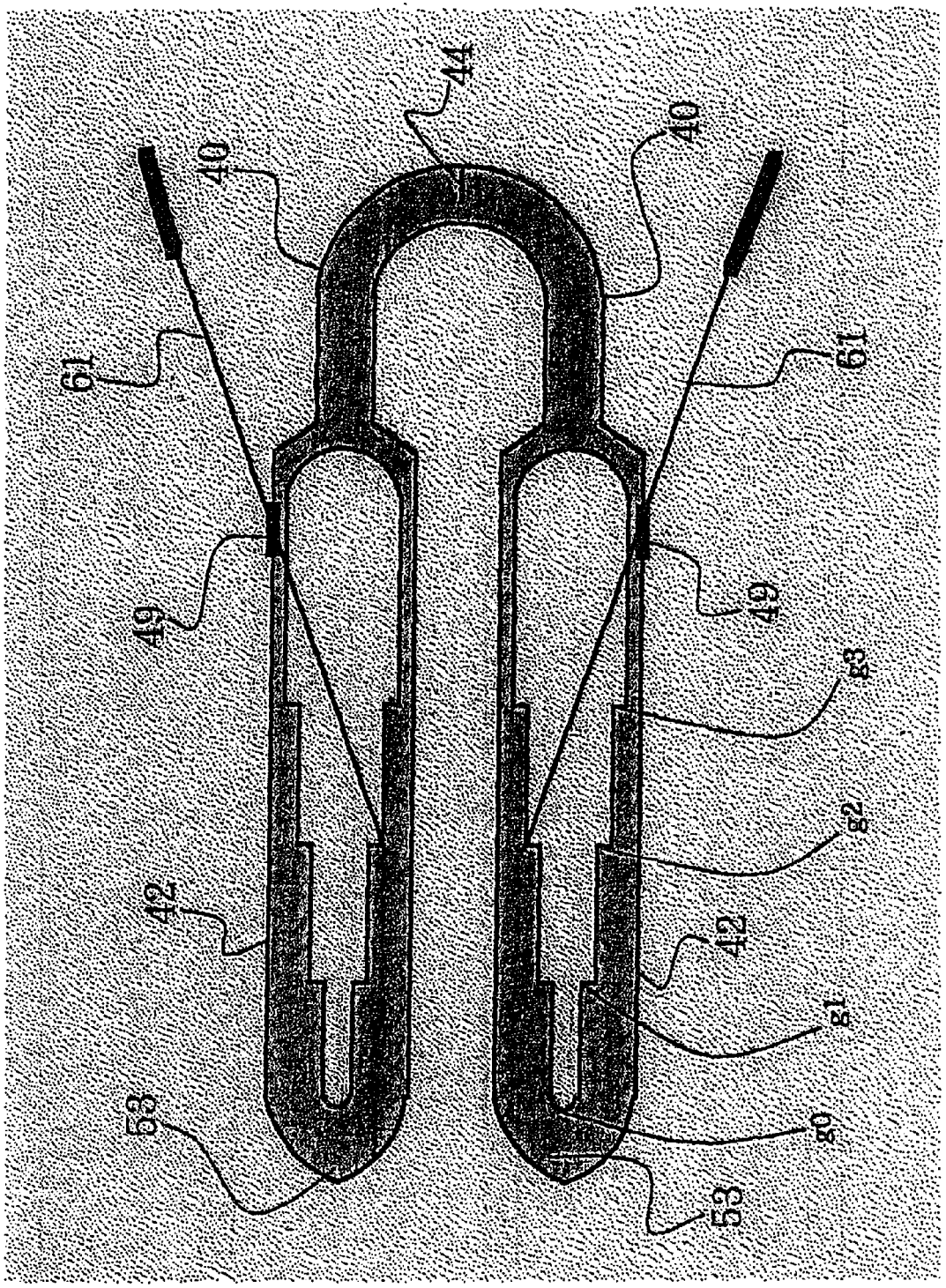
FIG. 7 is a sectional view showing an apparatus for intubation according to the present invention.
Figure 8:
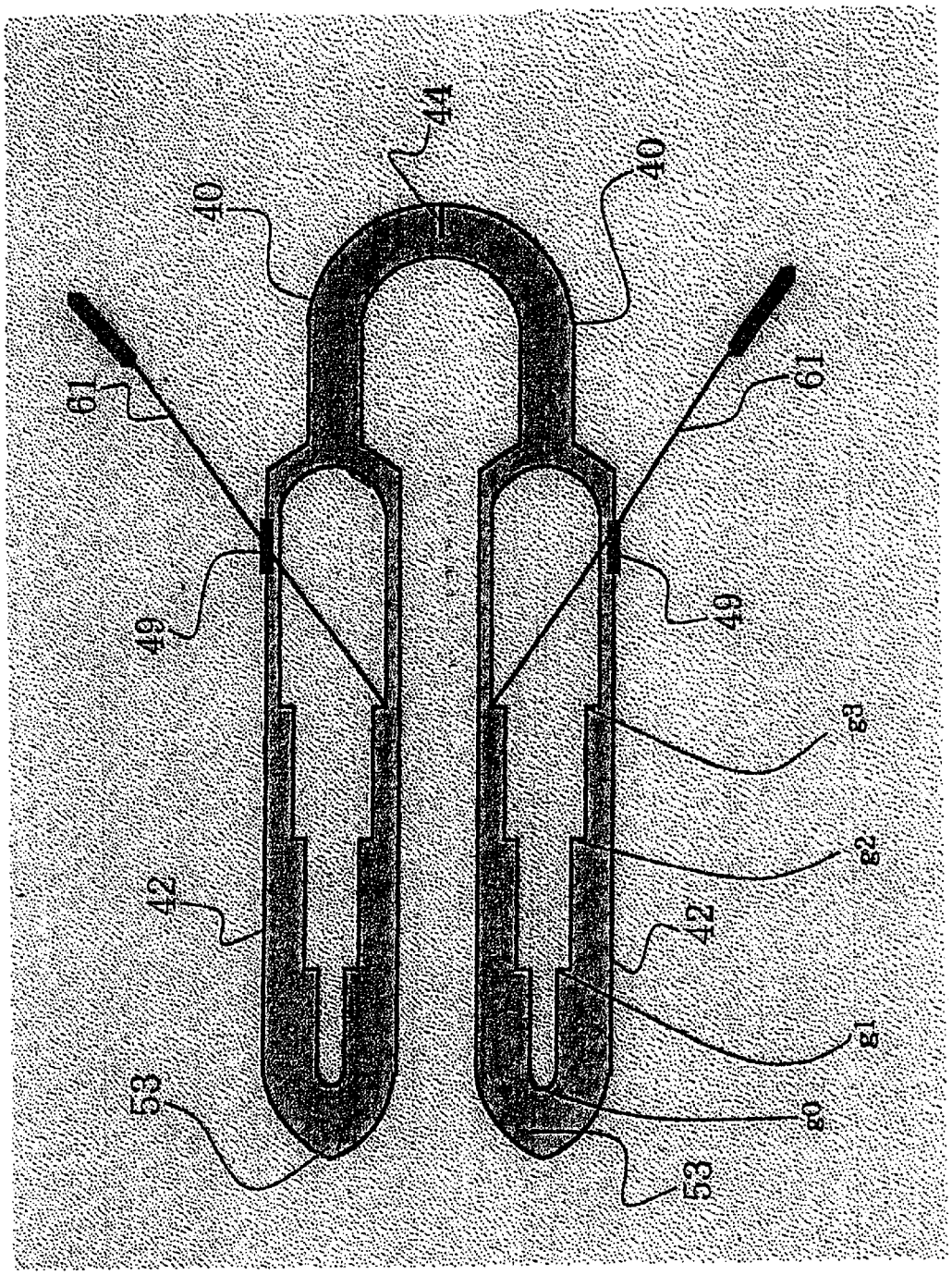
FIG. 8 is a sectional view showing an apparatus for intubation according to the present invention.

As shown in FIGS. 6, 7 and 8, the thicker tubes 42 can be pushed into the lacrimal duct by pushing the steps g1, g2 and g3 on the inner surface of the thicker tubes 42 with the tip of the probe 61.

Figure 9:
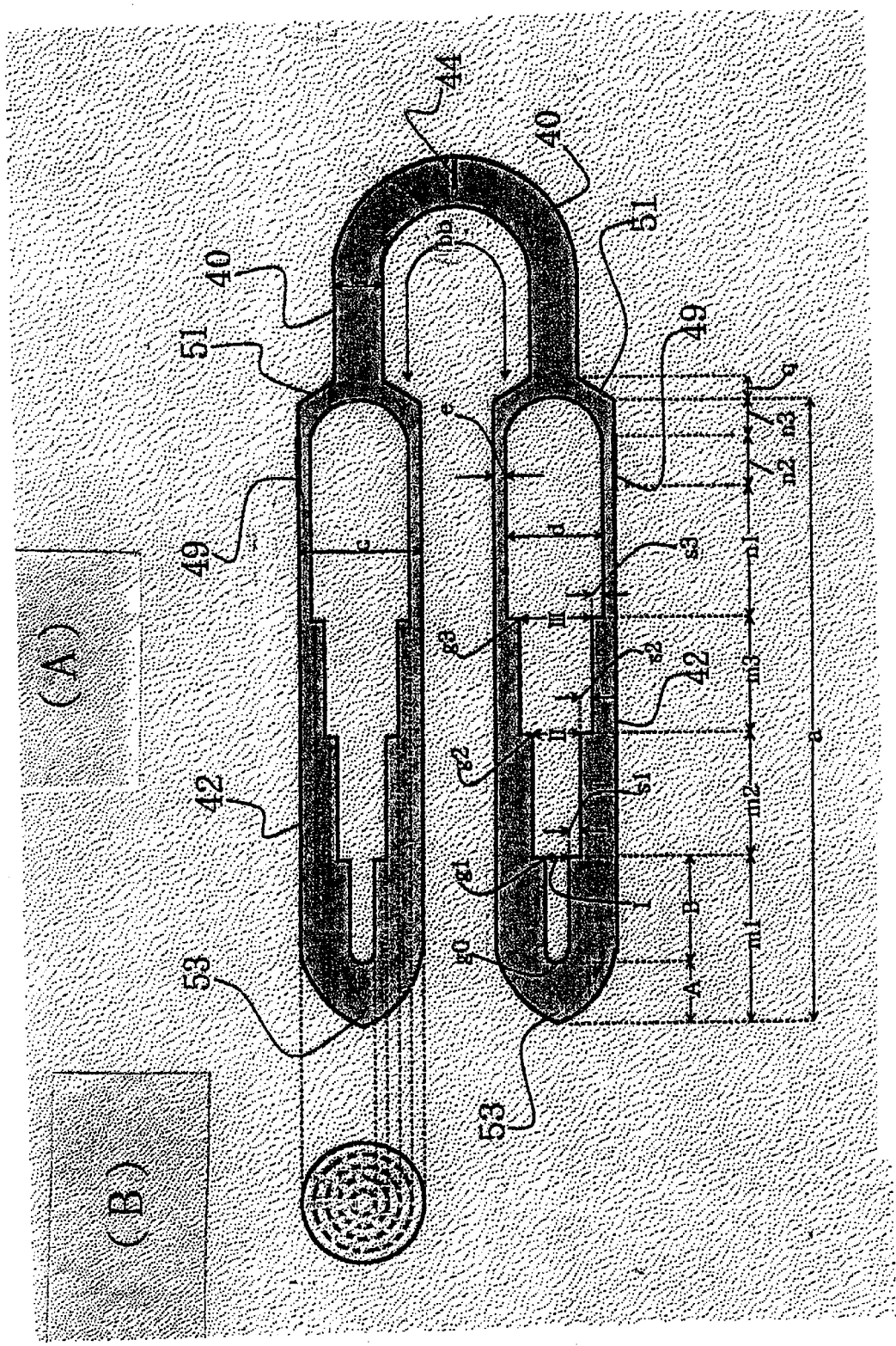
FIG. 9A is a sectional view showing an apparatus for intubation according to the present invention.
FIG. 9B is an end elevational view showing one end of an apparatus for intubation according to the present invention.
Figure 10:
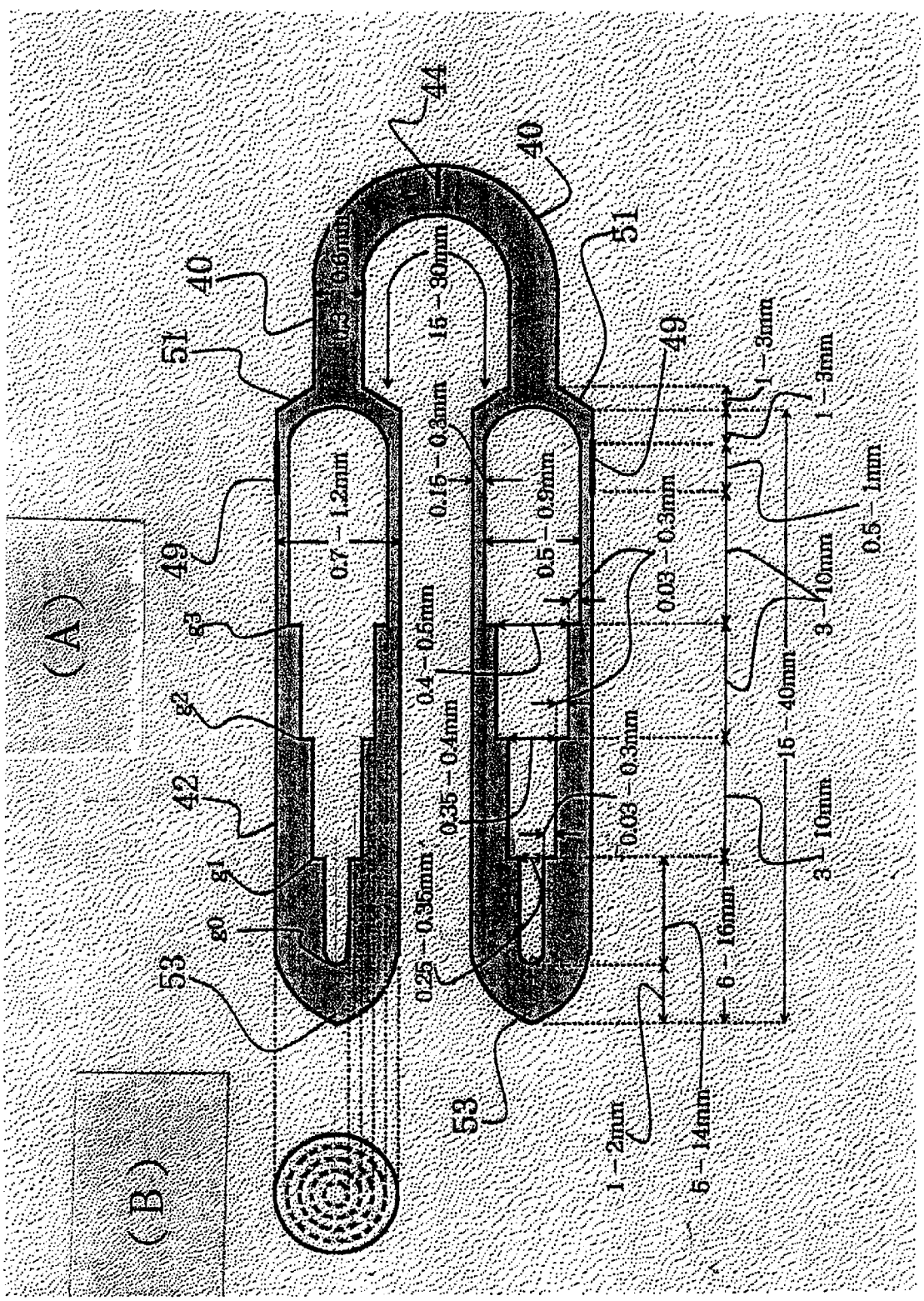
FIG. 10A is a sectional view showing an apparatus for intubation according to the present invention.
FIG. 10B is an end elevational view showing one end of an apparatus for intubation according to the present invention.

As shown in FIGS. 9 and 10, the length a of the thicker tube is 15~40 mm, the length bb of the thinner tube (or rod) is 15~30 mm, and the length q of the boundary portion 51 between the thicker tube 42 and the thinner tube (or rod) is 1~3 mm.

As shown in FIGS. 9 and 10, the outer diameter c of the thicker tube is 0.7~1.2 mm, the inner diameter I is 0.25~0.35 mm, the inner diameter II is 0.35~0.4 mm, the inner diameter III is 0.4~0.5 mm, and the inner diameter d is 0.5~0.9 mm. The outer diameter f of the thinner tube (or rod) is 0.3~0.6 mm.

As shown in FIGS. 9 and 10, the length A from the tip to closed end g0 is 1~2 mm, the length B from the closed end g0 to step g1 is 5~14 mm, and the length m1 from the tip to step g1 is 6~16 mm, the length m2 from the step g1 to step g2 is 3~10 mm, the length m3 from the step g2 to step g3 is 3~10 mm, the length n1 from the step g3 to small cut 49 is 3~10 mm, the length n2 of the small cut is 0.5~1 mm, and the length n3 from the small cut to other end of the thicker tube is 1~3 mm.

As shown in FIGS. 9 and 10, the wall thickness e of the thicker tube 42 is 0.15~0.3 mm, and the height of the step is 0.03~0.3 mm in any of the steps S1, S2 and S3.

Figure 11:
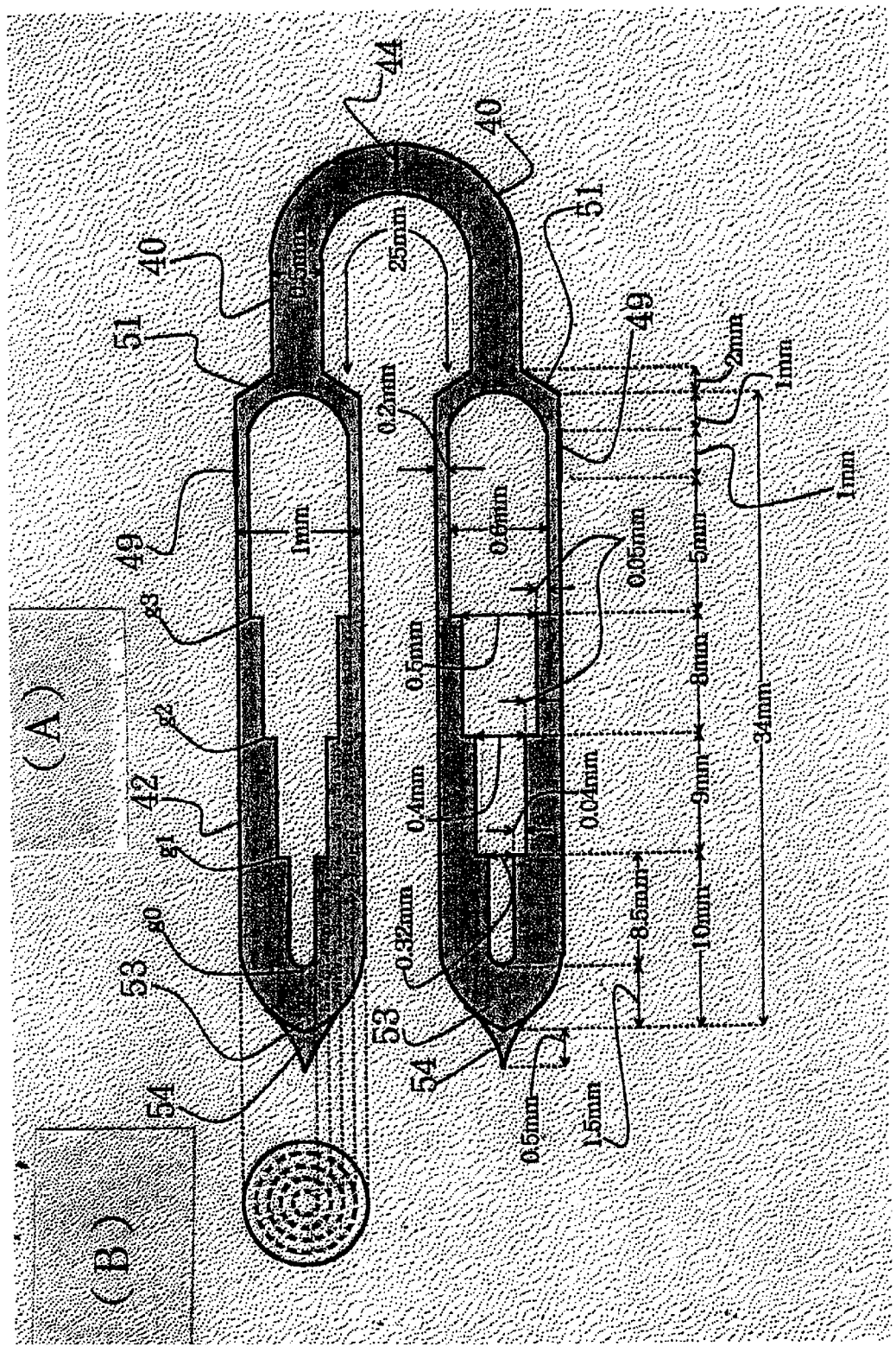
FIG. 11A is a sectional view showing an apparatus for intubation according to the present invention.
FIG. 11B is an end elevational view showing one end of an apparatus for intubation according to the present invention.

FIG. 11 shows a typical embodiment among many with step(s) shown in FIGS. 9 and 10. Although in FIGS. 9, 10 and 11, the number of steps in the thicker tube 42 is three: g1, g2 and g3, more or less than three is also useful.

Figure 12:
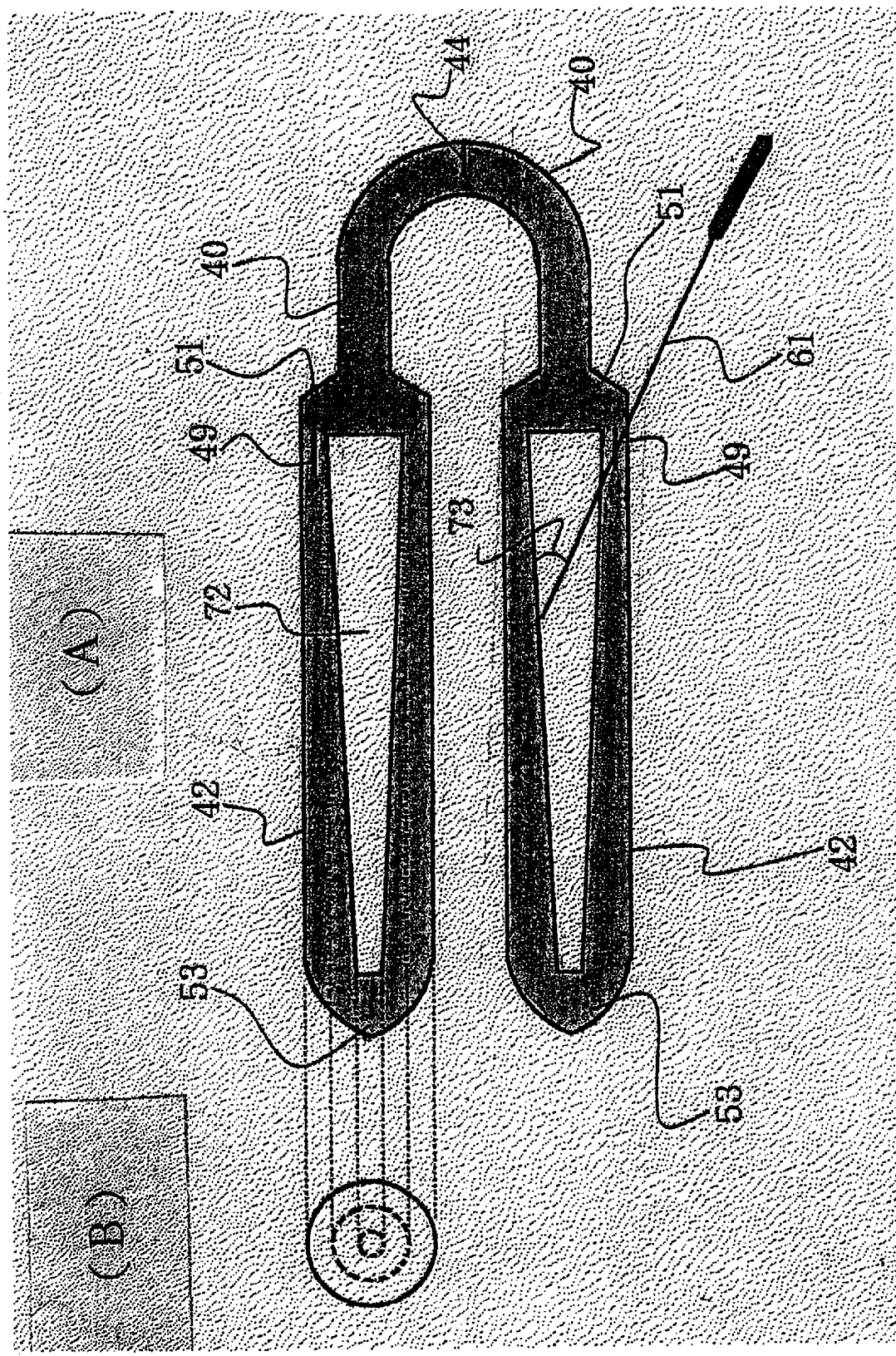
FIG. 12A is a sectional view showing an apparatus for intubation according to the present invention.
FIG. 12B is an end elevational view showing one end of an apparatus for intubation according to the present invention.
Figure 13:
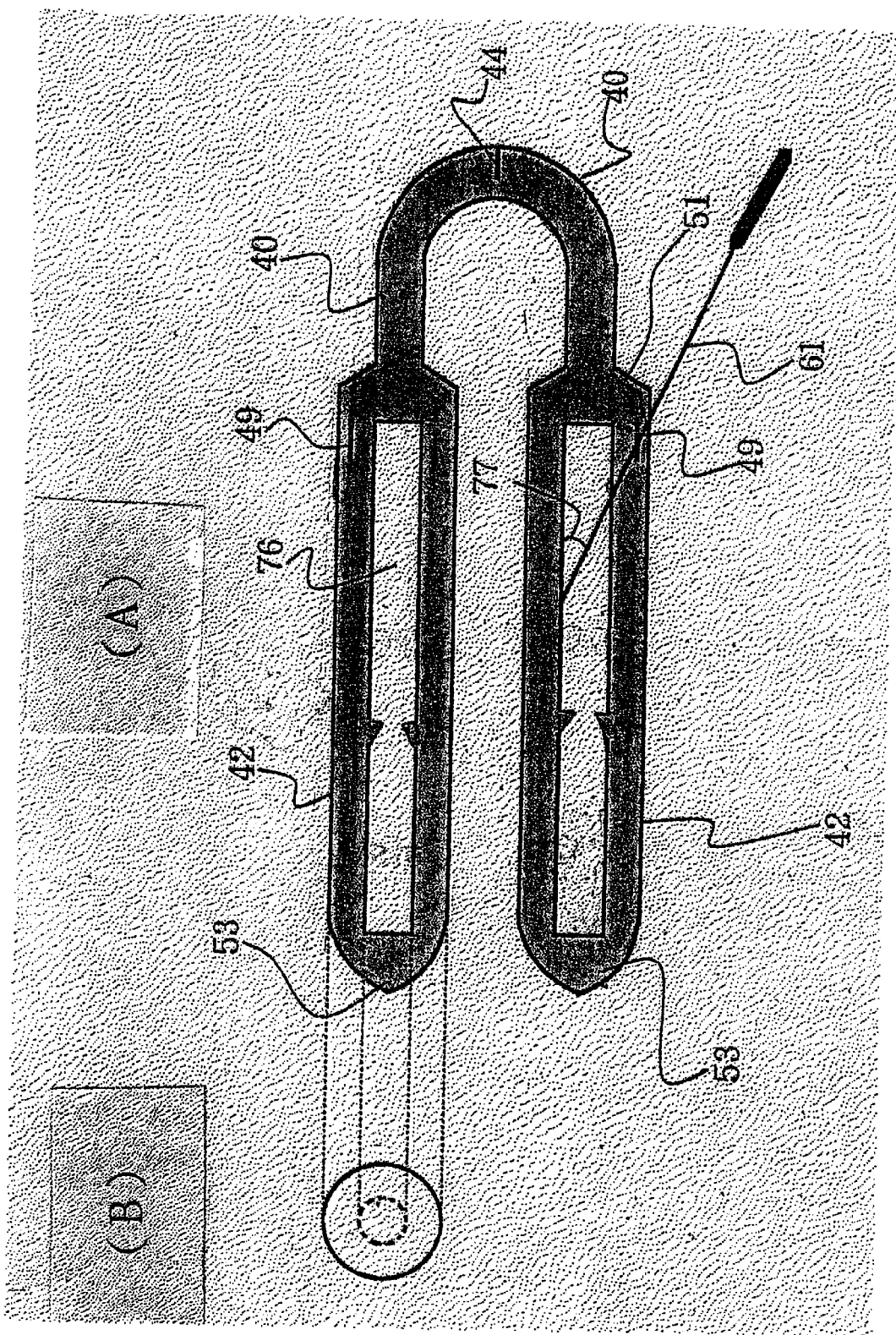
FIG. 13A is a sectional view showing an apparatus for intubation according to the present invention.
FIG. 13B is an end elevational view showing one end of an apparatus for intubation according to the present invention.

As shown in FIG. 12, if the shape of the inner space of the thicker tube is the frustum of the circular cone, a probe 61 can be pushed into the lacrimal duct easier. The reason for this is that because the angle 73 formed by the inner surface of the tube and the probe shown in FIG. 12 is greater than the angle 77 shown in FIG. 13, the tip of the probe can press the inner surface more effectively.

Figure 14:
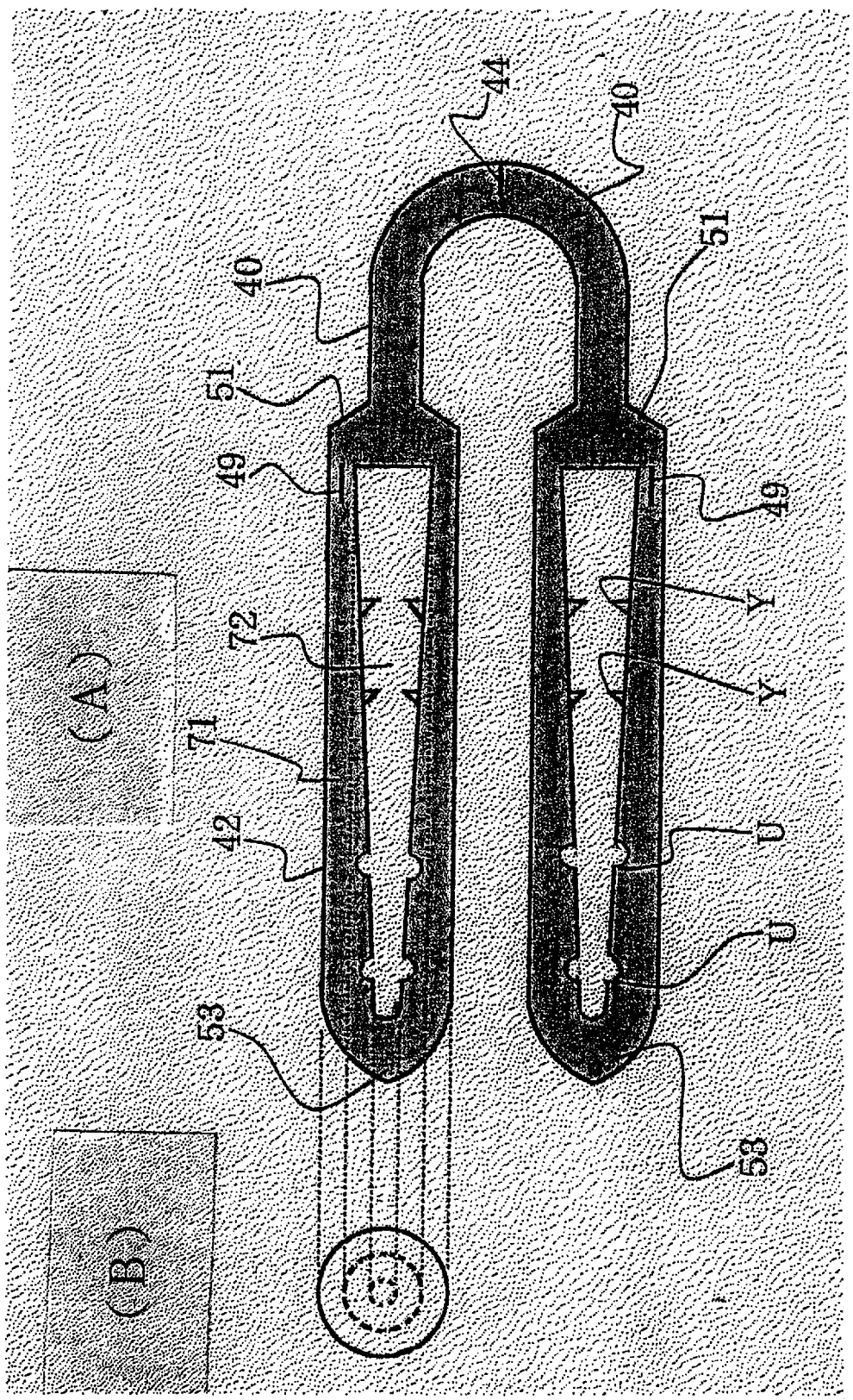
FIG. 14A is a sectional view showing other apparatus for intubation according to the present invention.
FIG. 14B is an end elevational view showing one end of an apparatus for intubation according to the present invention.

As shown in FIG. 14, if the protuberances Y and grooves U are applied to the inner surface 72 with the shape of the frustum of the circular cone of the thicker tube, the thicker tube 42 can be pushed into the lacrimal duct by the probe 61 more easily than the apparatus for intubation shown in FIGS. 12. Other irregular inner surface (not illustrated) is also useful for the thicker tube 42

Figure 15:
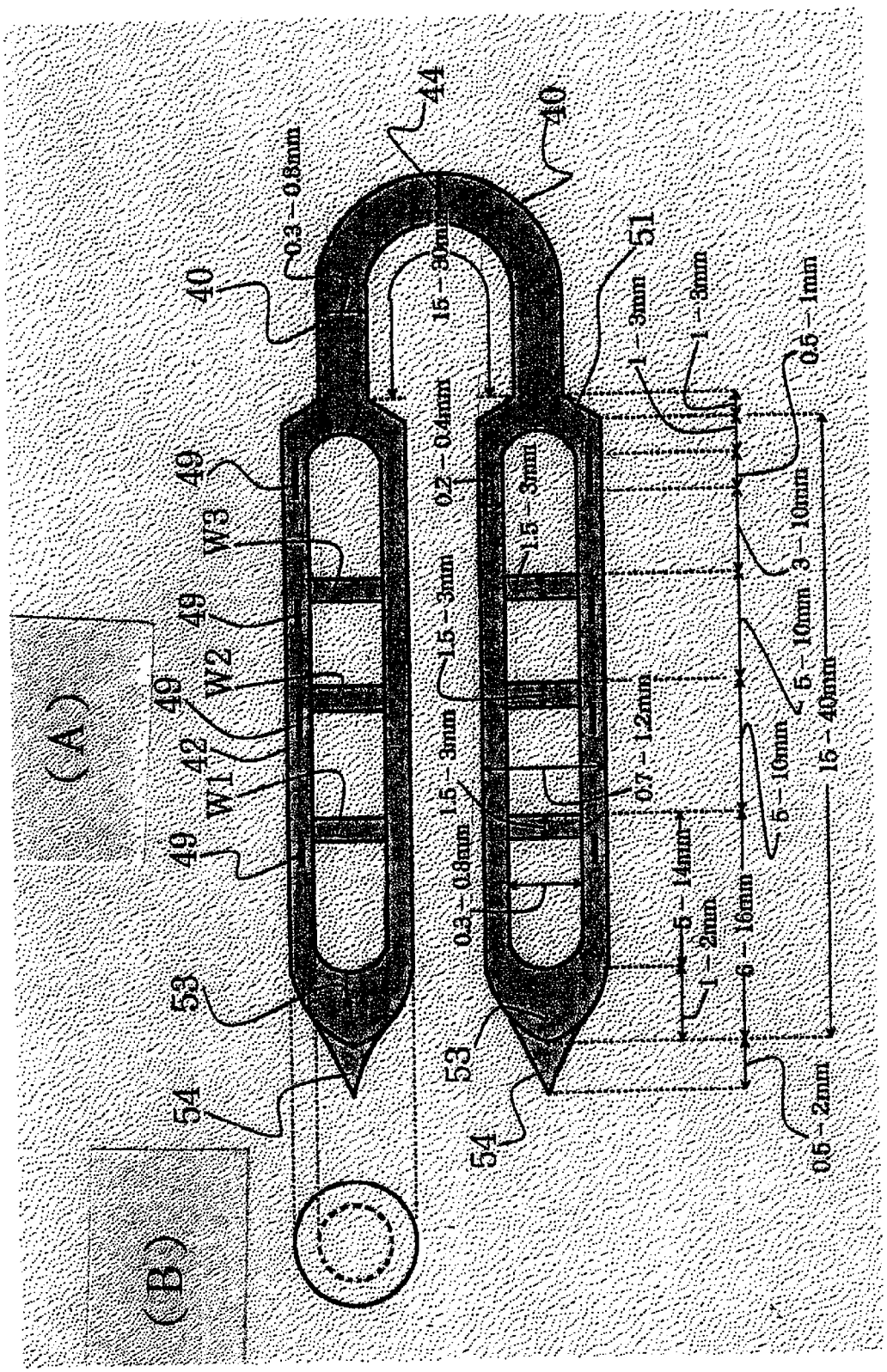
FIG. 15A is a sectional view showing other apparatus for intubation according to the present invention.
FIG. 15B is an end elevational view showing one end of an apparatus for intubation according to the present invention.

As shown in FIG. 15, by setting the septa W1, W2 and W3 in the thicker tubes like knot(s) of bamboo, the thicker tubes can be inserted into the lacrimal duct securely and easily by using a probe 61.

Figure 16:
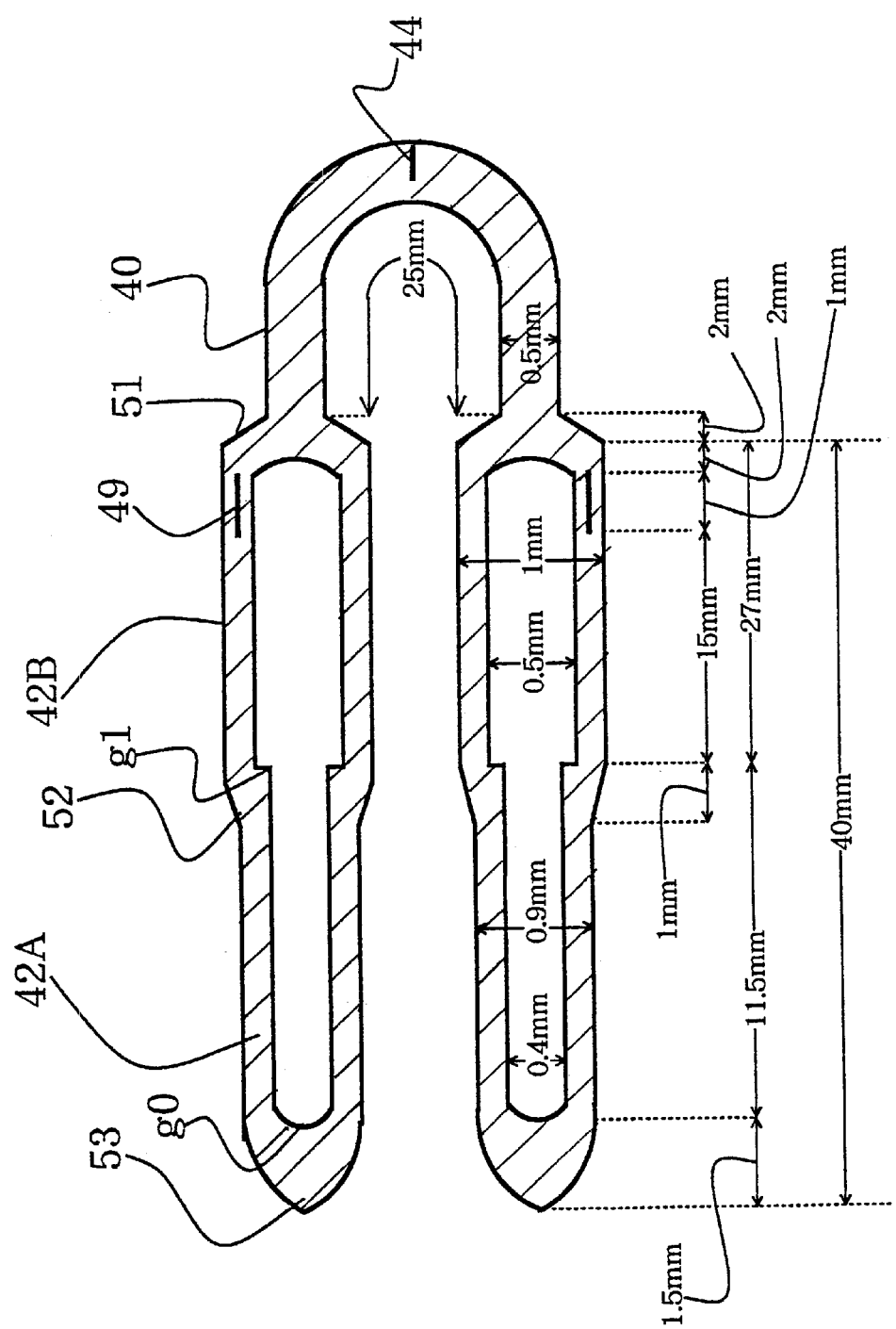
FIG. 16 is a sectional view showing other apparatus for intubation according to the present invention.

In the embodiment of FIG. 16 with a typical size, the thicker tube 42 consists of the anterior portion 42A and posterior portion 42B. The outer diameter of the anterior portion 42A is 0.1~0.3 mm smaller than that of the posterior portion 42B. There is a slope 52 and step g1 between the two different sized tubes 42A and 42B.

Figure 17:
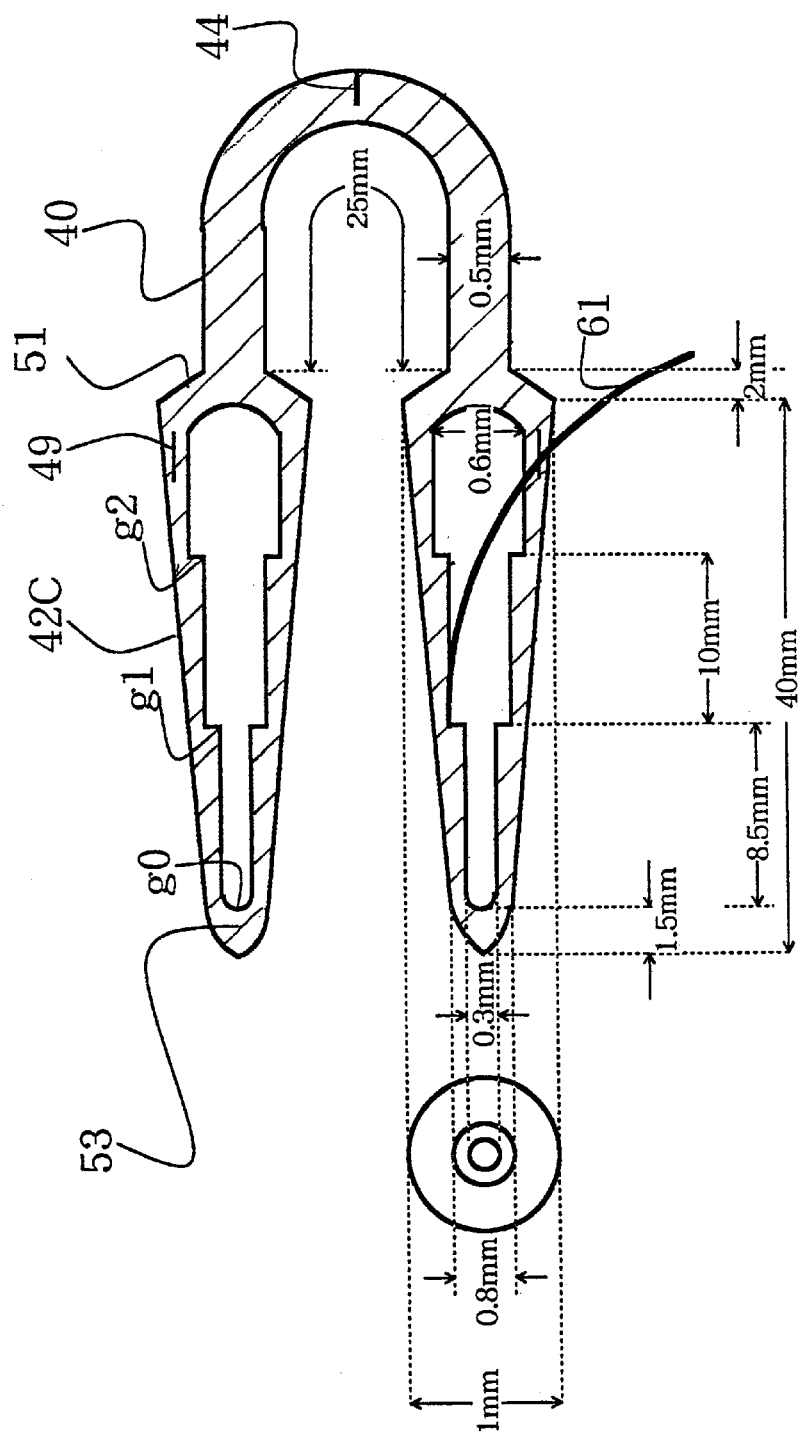
FIG. 17A is a sectional view showing other apparatus for intubation according to the present invention.
FIG. 17B is an end elevational view showing one end of an apparatus for intubation according to the present invention.

In the embodiment shown in FIG. 17 with a typical size, the carrot thicker tubes 42C are in the shape of a carrot and have the steps g1, g2. The different sized tubes 42A, 42B in FIG. 16 and the carrot thicker tubes 42C in FIG. 17 can be more easily inserted into the lacrimal duct than the thicker tube 42 in FIGS. 1~15.

Figure 18:
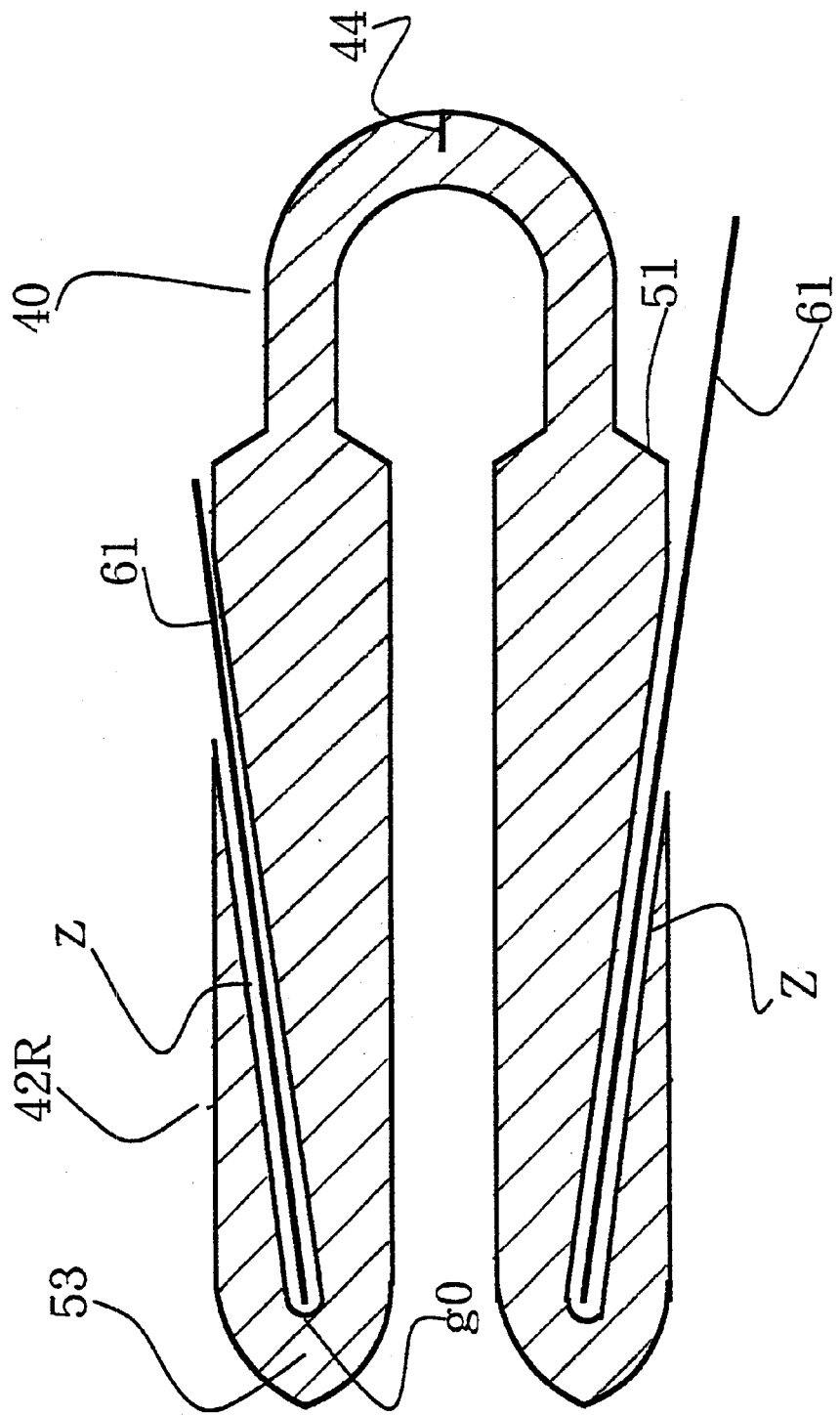
FIG. 18 is a sectional view showing other apparatus for intubation according to the present invention.

In the embodiment shown in FIG. 18, the thicker rods 42R are connected with a thinner rod 40. The thicker rods 42R have a hole Z for a probe 61 to be inserted. The thicker rods 42R have the same size and shape as the thicker tube in FIGS. 1~15.

The different sized thicker rods which have the same size and shape as the different sized thicker tubes 42A, 42B are also useful (not illustrated).

Figure 19:
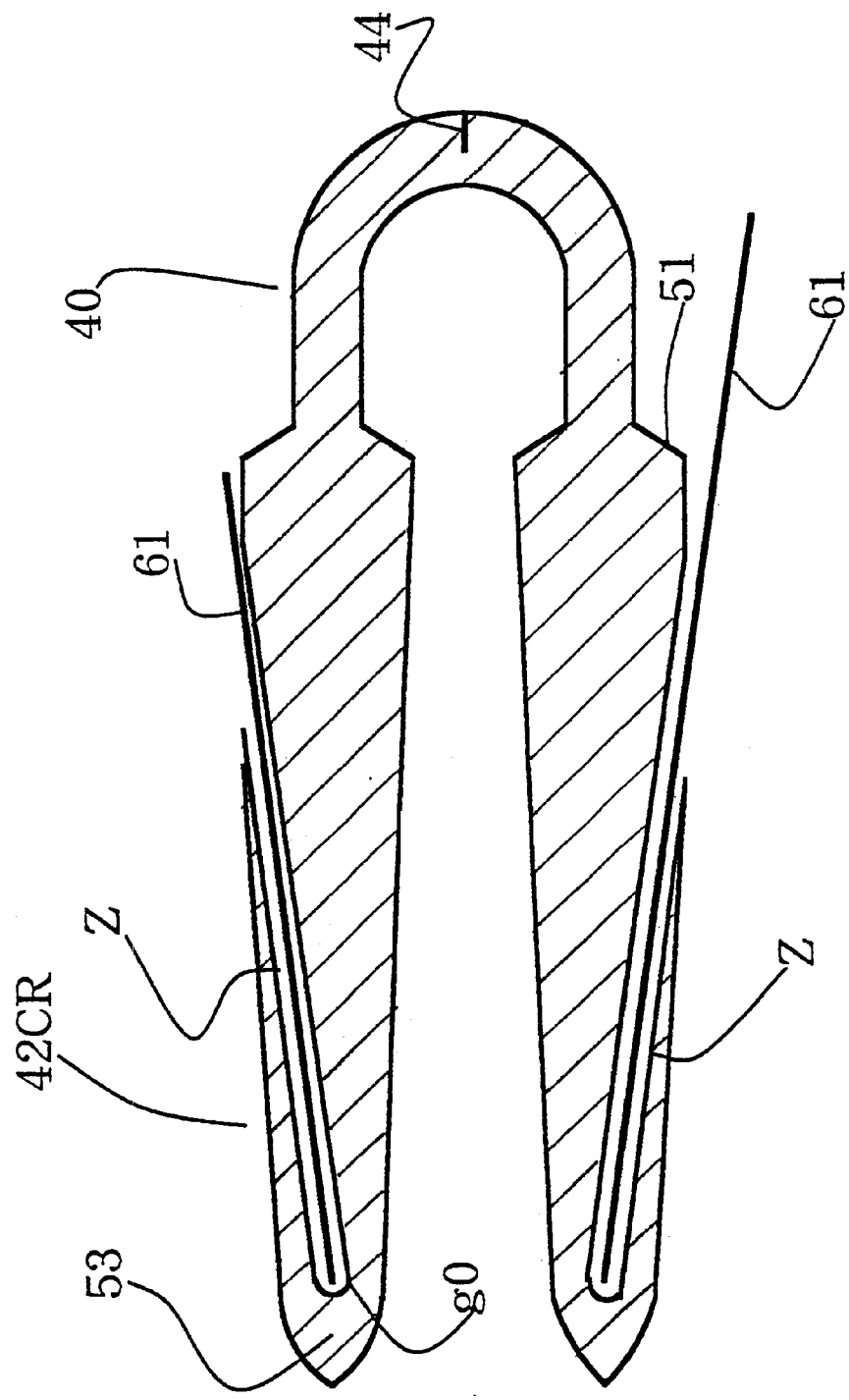
FIG. 19 is a sectional view showing other apparatus for intubation according to the present invention.

In the embodiment shown in FIG. 19, the carrot thicker rods 42CR are connected with the thinner rod 40. The carrot thicker rods 42CR are in the shape of a carrot and have a hole Z for a probe to be inserted.

Figure 20:
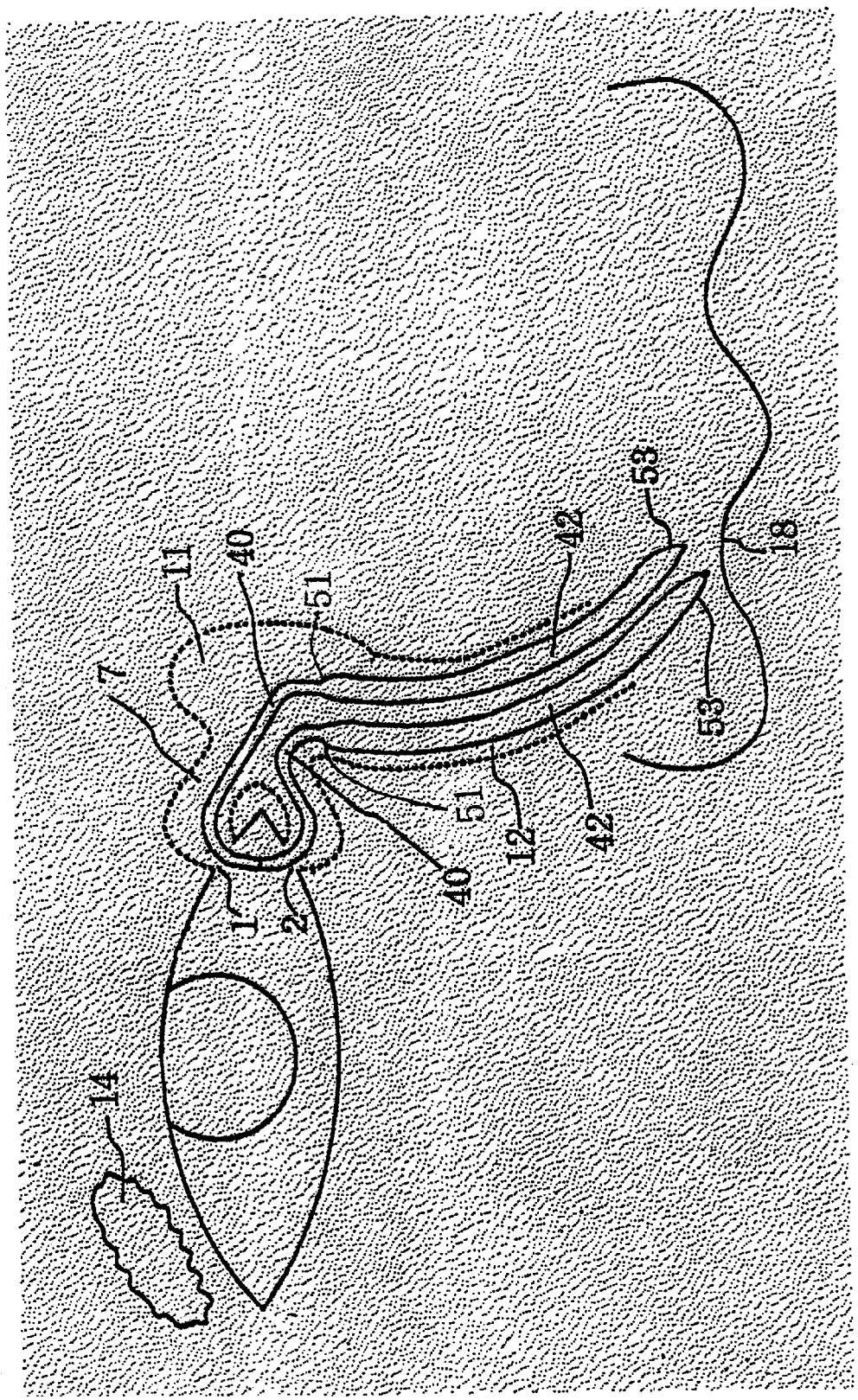
FIG. 20 is an explanatory diagram showing bicanalicular intubation according to the present invention.

FIG. 20 shows an instance of the state of the present invention which is inserted into the lacrimal duct.

Figure 21:
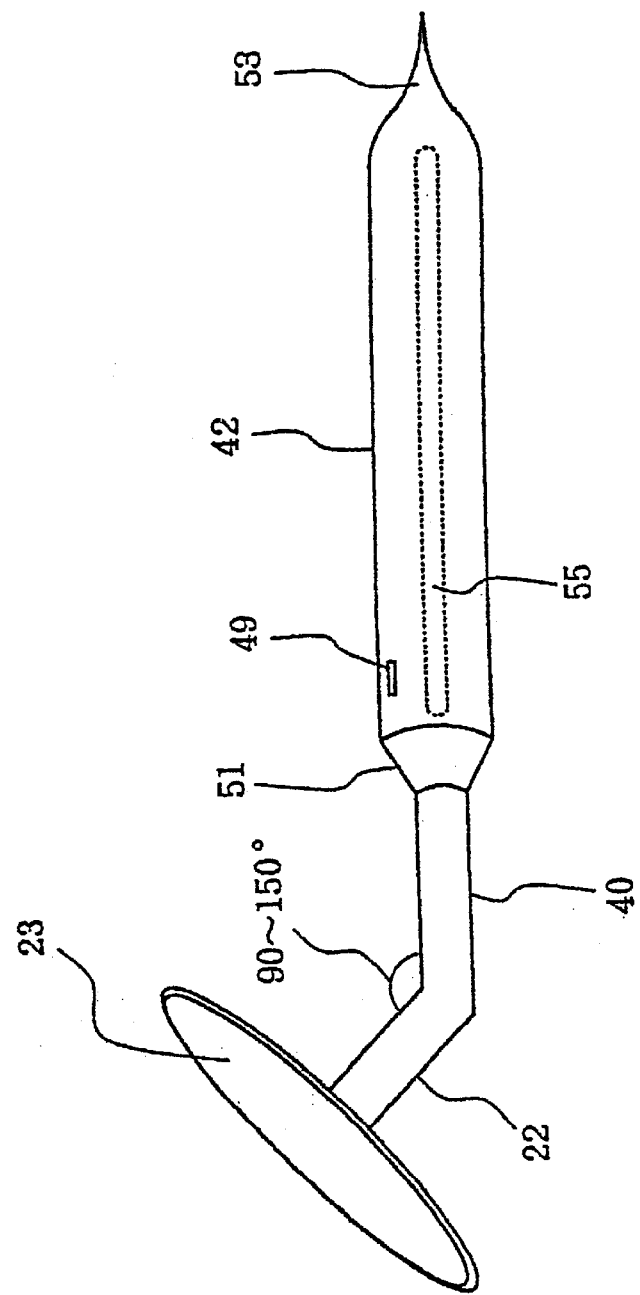
FIG. 21 is a perspective view showing an apparatus for monocanalicular intubation shown in Japanese Patent Publication No. 10-256109.
Figure 22:
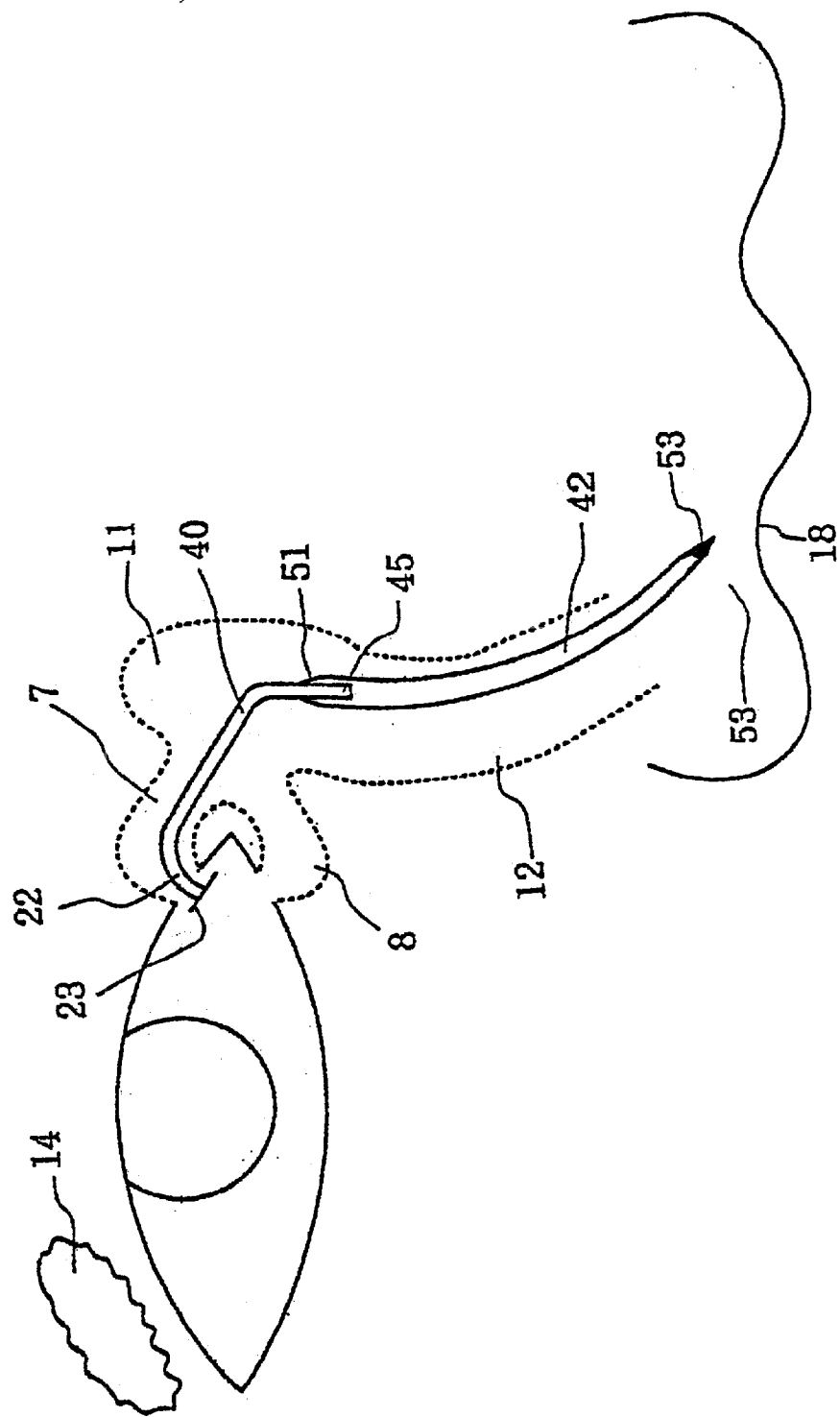
FIG. 22 is an explanatory diagram showing monocanalicular intubation shown in Japanese Patent Publication No. 10-256109.
Figure 23:
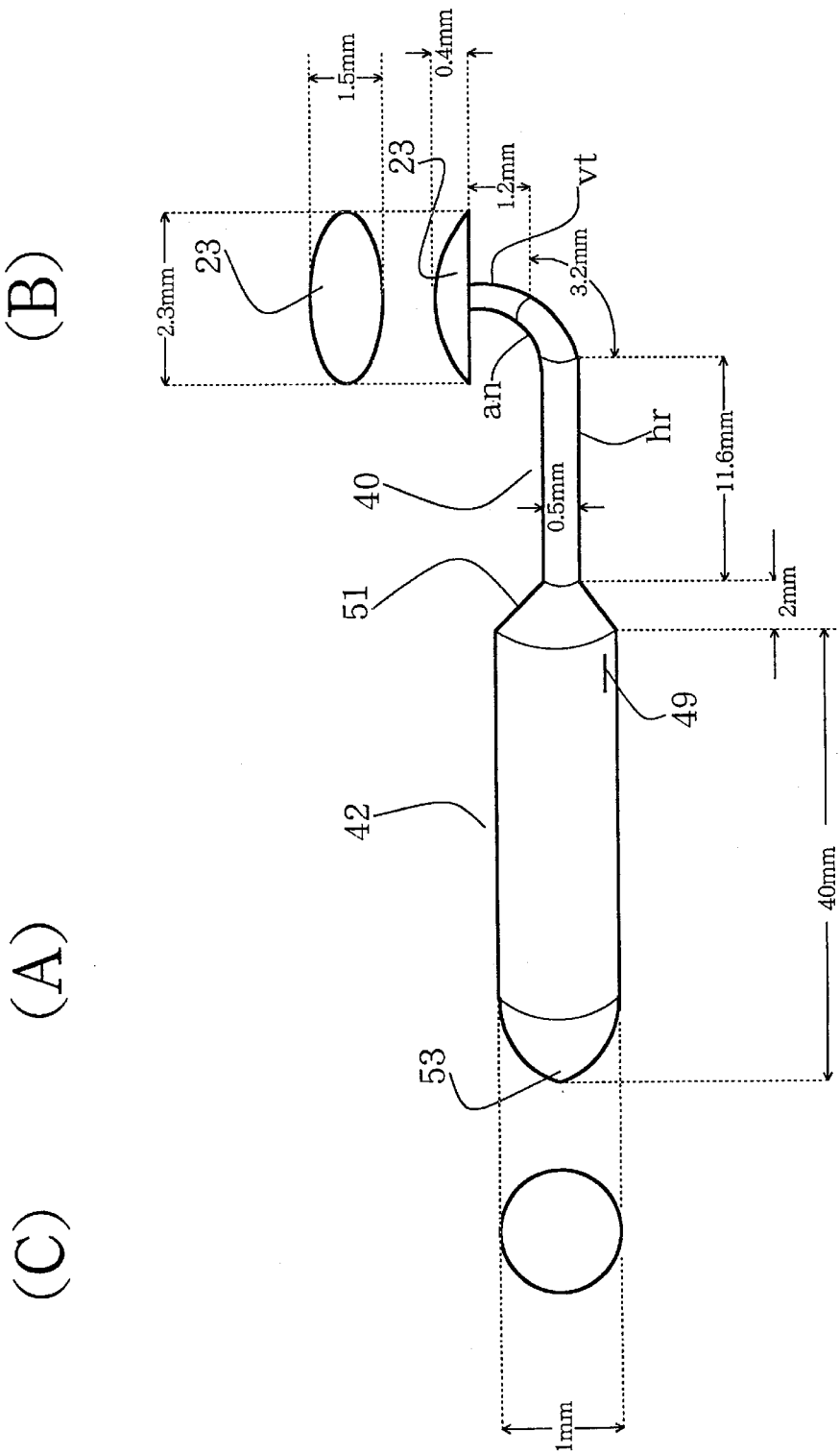
FIG. 23A is a perspective view showing an apparatus for intubation according to the present invention.
FIG. 23B is an end elevational view showing one end of an apparatus for intubation according to the present invention.
FIG. 23C is an end elevational view showing one end of an apparatus for intubation according to the present invention.
Figure 24:
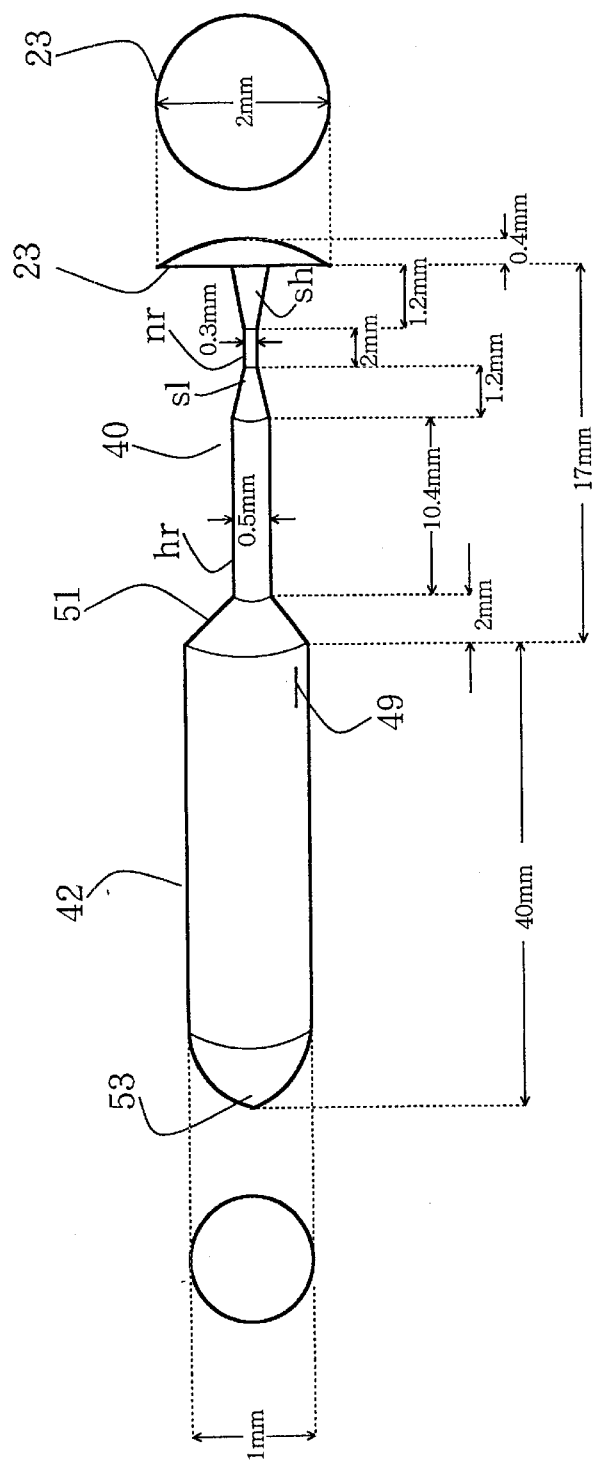
FIG. 24A is a perspective view showing an apparatus for intubation according to the present invention.
FIG. 24B is an end elevational view showing one end of an apparatus for intubation according to the present invention.
FIG. 24C is an end elevational view showing one end of an apparatus for intubation according to the present invention.

The thicker tubes (or rods) 42, 42C, 42A, B, 42R, 42CR in FIGS. 4~19 can be used as the thicker tube 42 for monocanalicular intubation, for example, in FIGS. 21 and 22 as shown in Japanese Patent Publication No. 10-256109 and FIGS. 23 and 24 with typical size and shape which are other apparatus for monocanalicular intubation according to the present invention.

Figure 2:
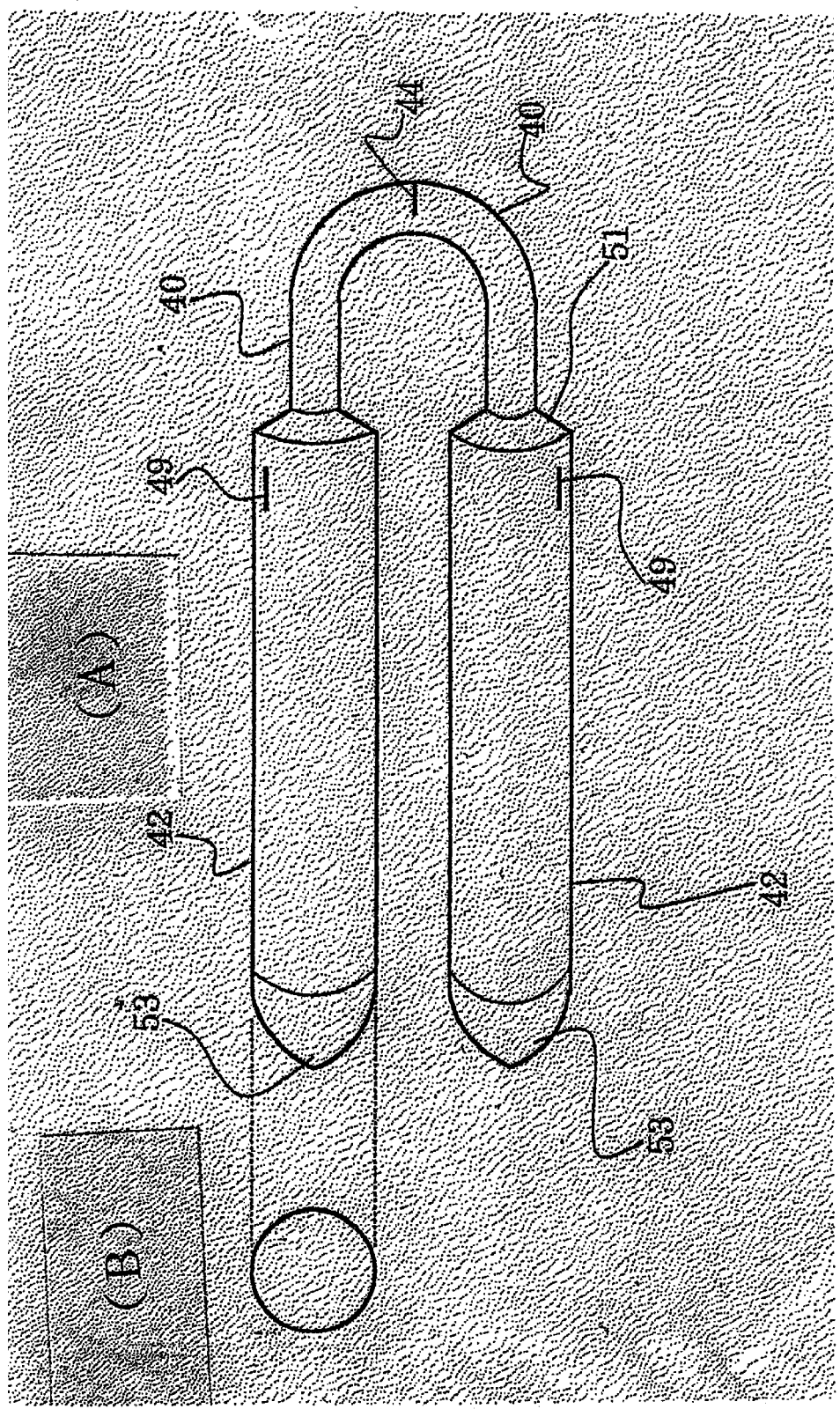
FIG. 2 is a perspective view showing a conventional nunchaku-style tube.
Figure 25:
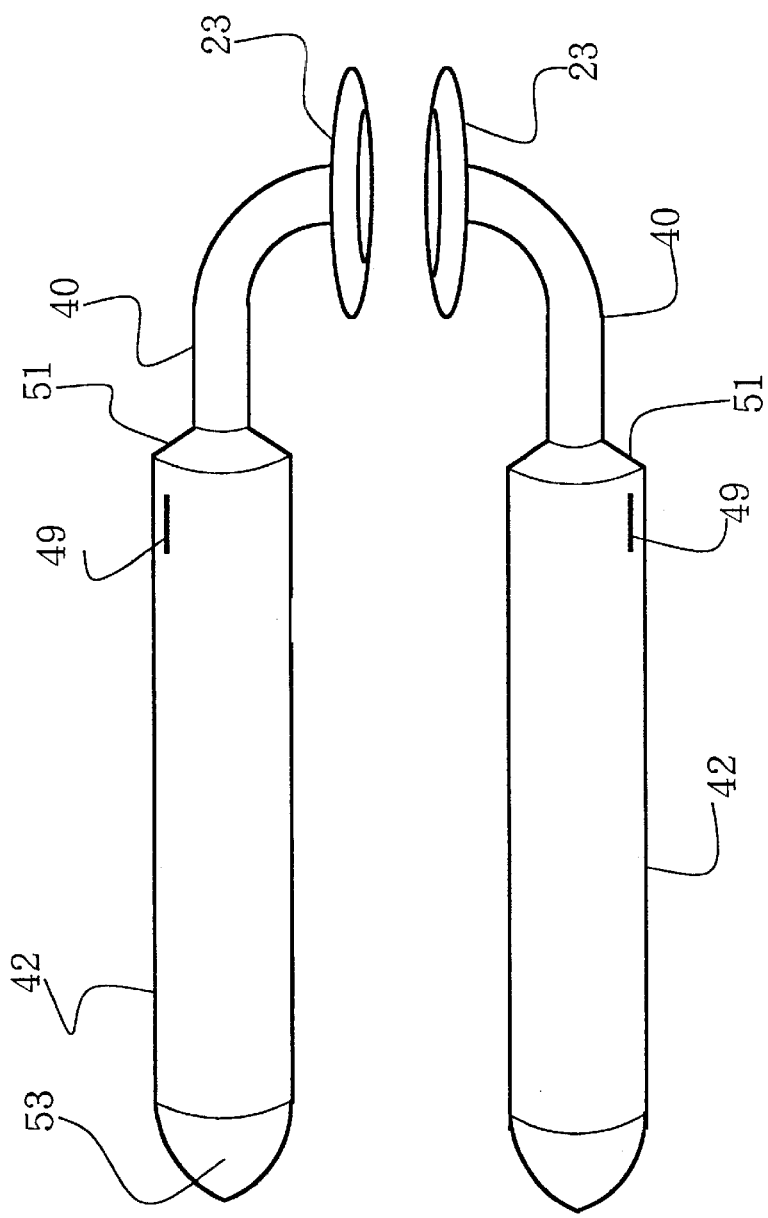
FIG. 25 is a perspective view showing an apparatus for intubation according to the present invention.
Figure 26:
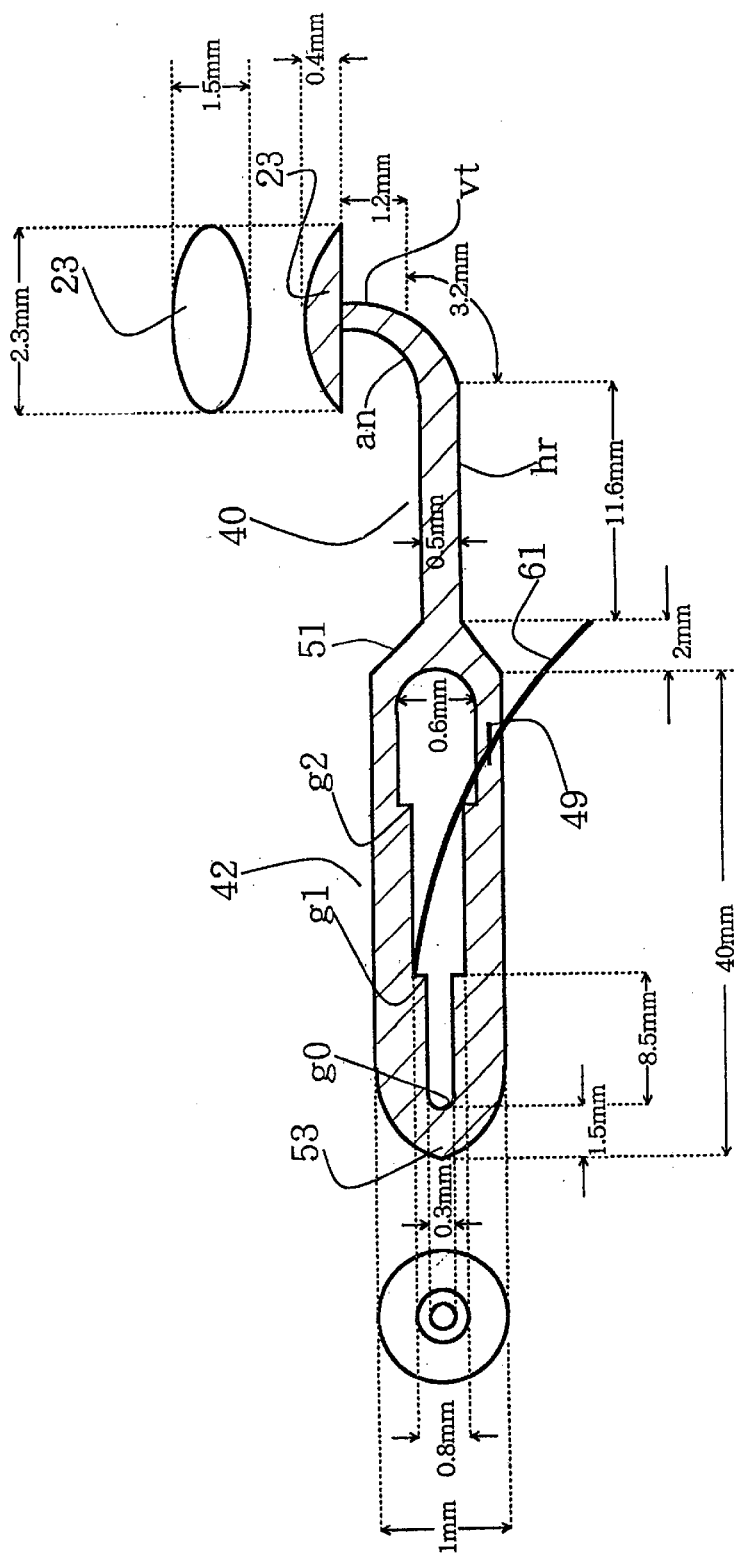
FIG. 26A is a sectional view showing an apparatus for intubation according to the present invention.
FIG. 26B is an and elevational view showing one end of an apparatus for intubation according to the present invention.
FIG. 26C is an and elevational view showing one end of an apparatus for intubation according to the present invention.
Figure 27:
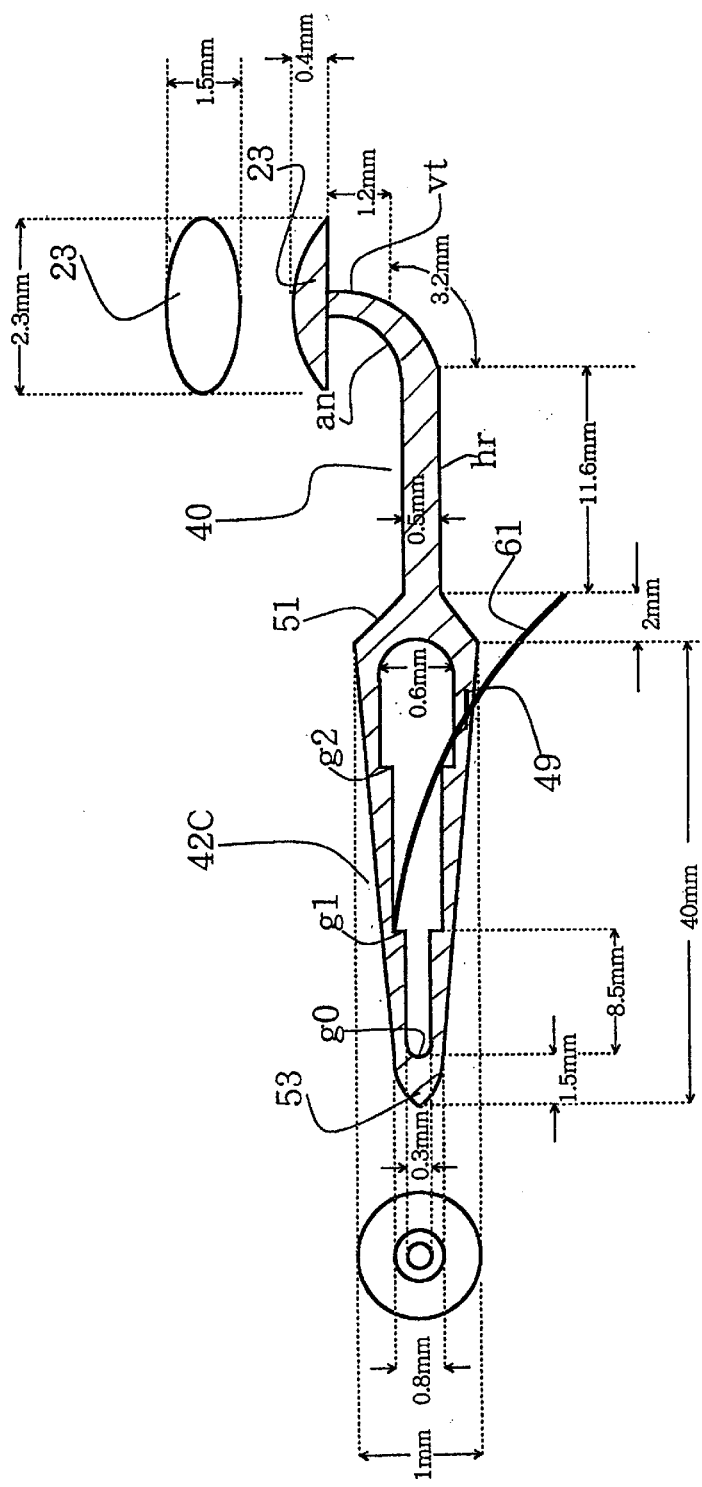
FIG. 27A is a sectional view showing an apparatus for intubation according to the present invention.
FIG. 27B is an end elevational view showing one end of an apparatus for intubation according to the present invention.
FIG. 27C is an end elevational view showing one end of an apparatus for intubation according to the present invention.
Figure 28:
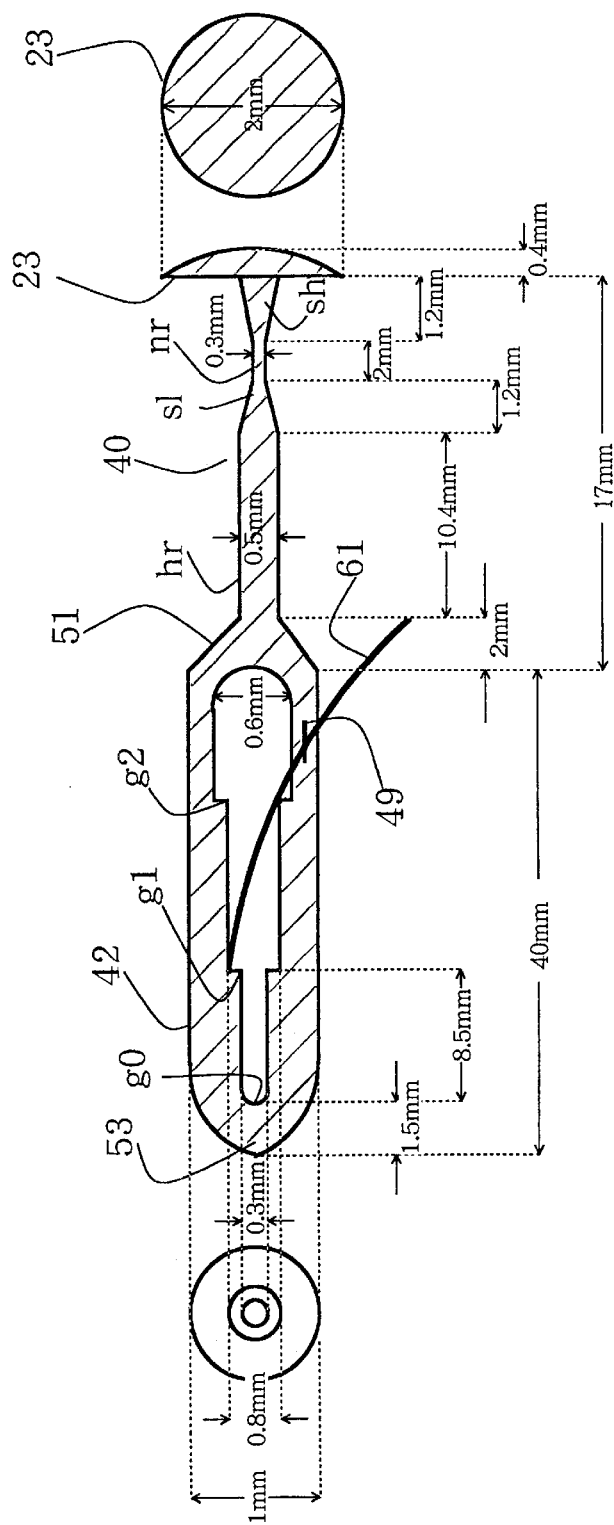
FIG. 28A is a sectional view showing an apparatus for intubation according to a present invention.
FIG. 28B is an end elevational view showing one end of an apparatus for intubation according to the present invention.
FIG. 28C is an end elevational view showing one end of an apparatus for intubation according to the present invention.
Figure 29:
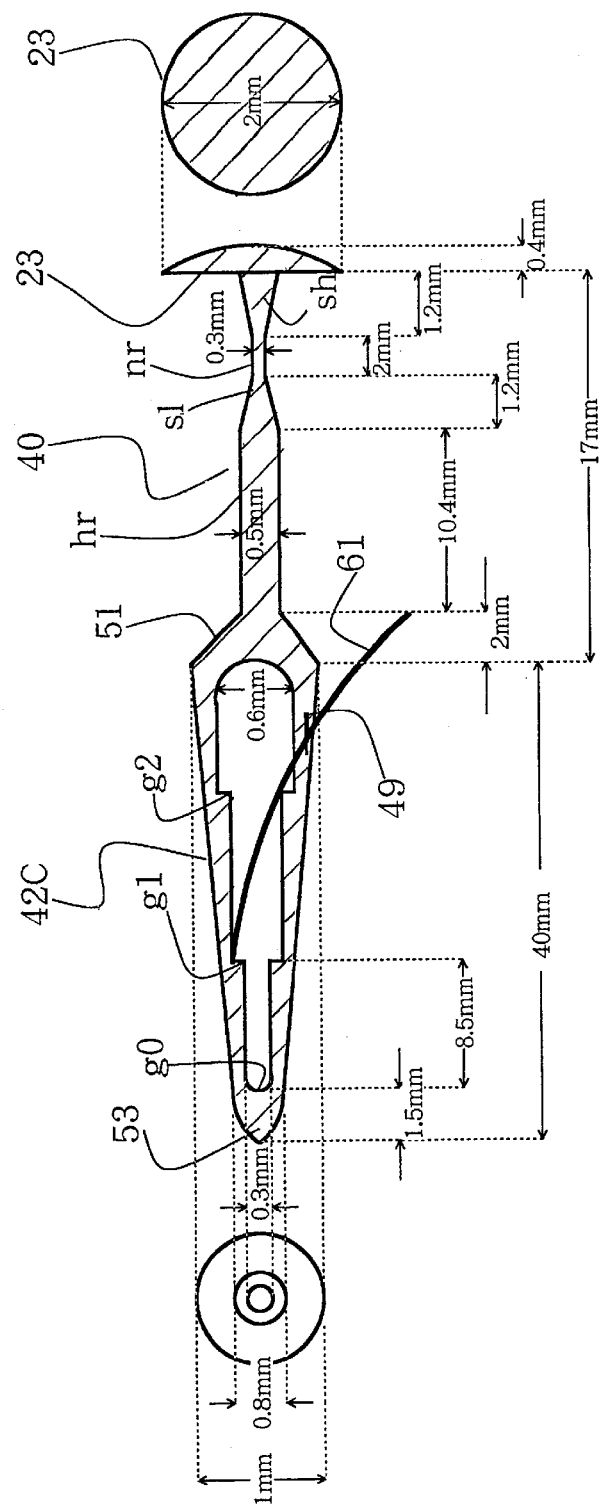
FIG. 29A is a sectional view showing an apparatus for intubation according to the present invention.
FIG. 29B is an end elevational view showing one end of an apparatus for intubation according to the present invention.
FIG. 29C is an end elevational view showing one end of an apparatus for intubation according to the present invention.
Figure 30:
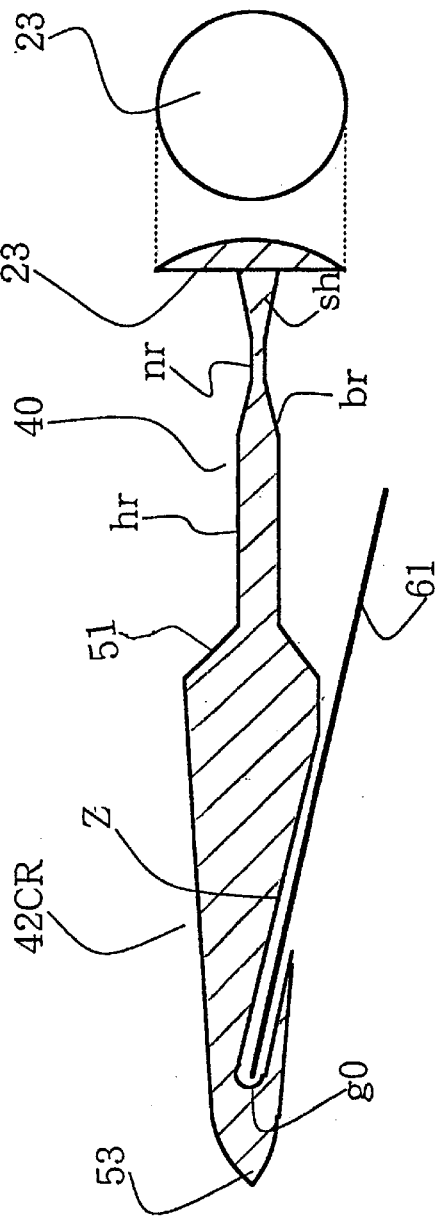
FIG. 30A is a sectional view showing an apparatus for intubation according to the present invention.
FIG. 30B is an and elevational view showing one end of an apparatus for intubation according to the present invention.

As shown in FIG. 25, the apparatus in FIGS. 21~24 are designed based on the nunchaku style tubing in FIG. 2 and consists of a half part of the nunchaku style tubing and a brim 23 which is glued with the end of the thinner tube (or rod) 40.

And FIGS. 26~30 with typical size and shape show an apparatus for monocanalicular intubation according to the present invention. In the embodiments shown in FIGS. 23, 26 and 27, the thinner rod 40 16 mm in length consists of the horizontal segment hr 11.6 mm in length, curved segment an 3.2 mm in length and vertical segment vt 1.2 mm in length and the end of the latter is glued with the brim 23.

In FIGS. 24 and 28~30 with typical size, the thinner rod 40 15 mm in length consists of the horizontal segment hr 10.4 mm in length, slope sl 1.2 mm in length, narrow segment nr 2 mm in length and short segment sh 1.2 mm in length.

FIG. 22 shows an instance of the state of the present invention in FIGS. 23~30 which is inserted into the lacrimal duct from the upper punctum.

As shown in FIGS. 20 and 22, the boundary portion 51 must be positioned in the lacrimal sac—nasolacrimal duct for the stability of the apparatus in the lacrimal duct.

Figure 31:
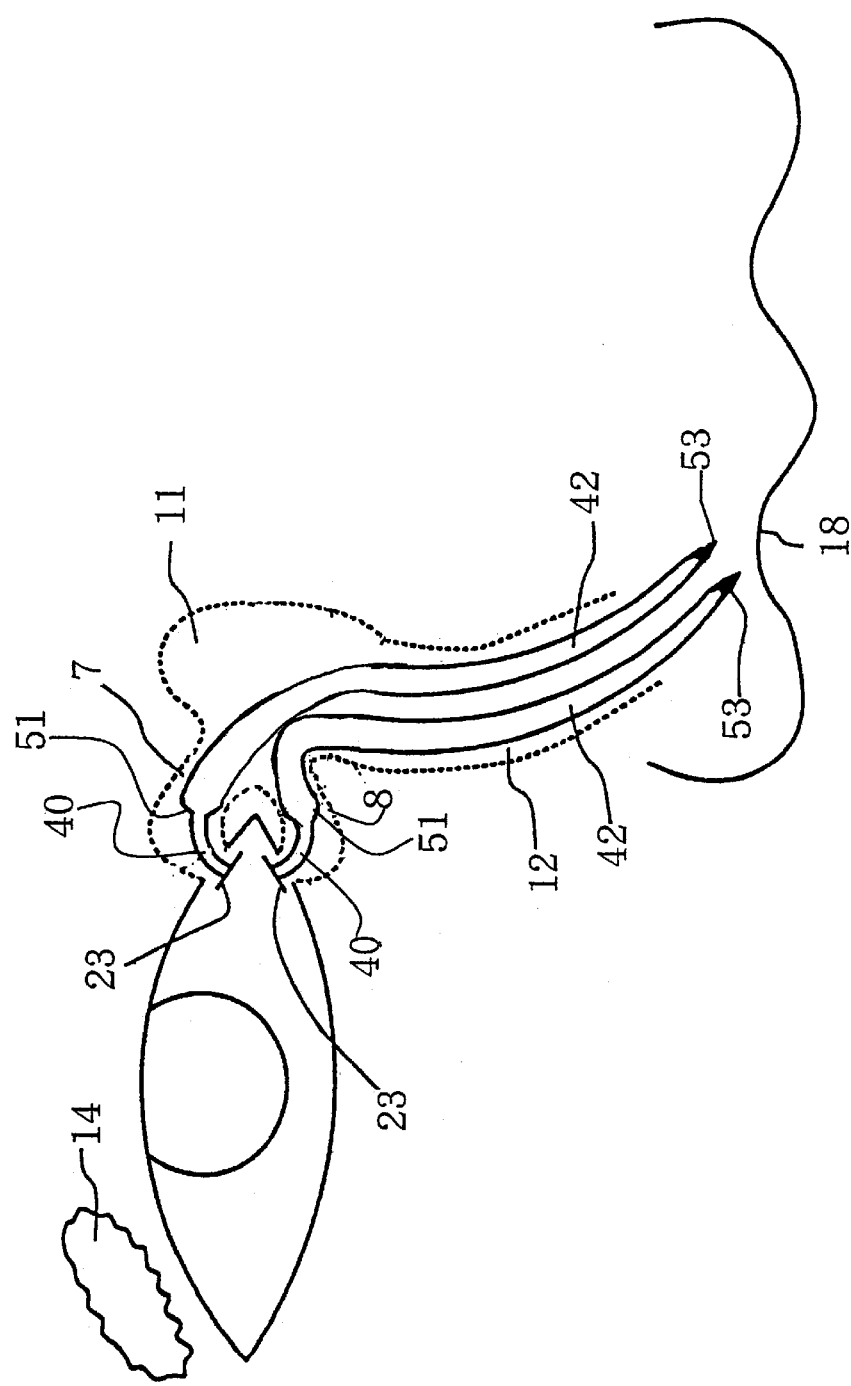
FIG. 31 is an explanatory diagram showing a previous apparatus for intubation.

The canalicular length of an adult is 10~15 mm with an avarage of 11 mm (for example see Kurihashi K:Dacryology, Medical A01 shuppan Inc., Tokyo, 1998),. Therefore, the thinner tube (or rod) 40 in FIG. 20 must be 20~30 mm or more in length for adults, and the thinner tube (or rod) 40 in FIG. 22 must be 10~15 mm or more for adults. If the boundary portion 51 is positioned in the canaliculus as shown in FIG. 31, the apparatus are not stable in the lacrimal duct and easily dislocate.

The length of the thinner tube (or rod) in FIG. 22 is more than the canalicular length to get better stability in the lacrimal duct. By doing so, the boundary portion 51 between the thinner tube (or rod) 40 and thicker tube (or rod) 42 positioned in the lacrimal sac—nasolacrimal duct 11, 12 which runs perpendicularly and slight posteriorly and thinner tube (or rod) 40 in the horizontal part of the canaliculus 7,8 which runs horizontally and is pulled by the thicker tube (or rod) with the help of gravity, results in good stability in the lacrimal duct without fixation like the nunchaku style tube shown in FIG. 20.

The thicker tube (or rod) 42 is heavier than the thinner tube (or rod) 40. With the pulling effect of the thicker tube (or rod) 42, the brim 23 in FIGS. 21~30 presses the punctum and prevents tear fluid from entering the punctum (the opening of the canaliculus).

Figure 3:
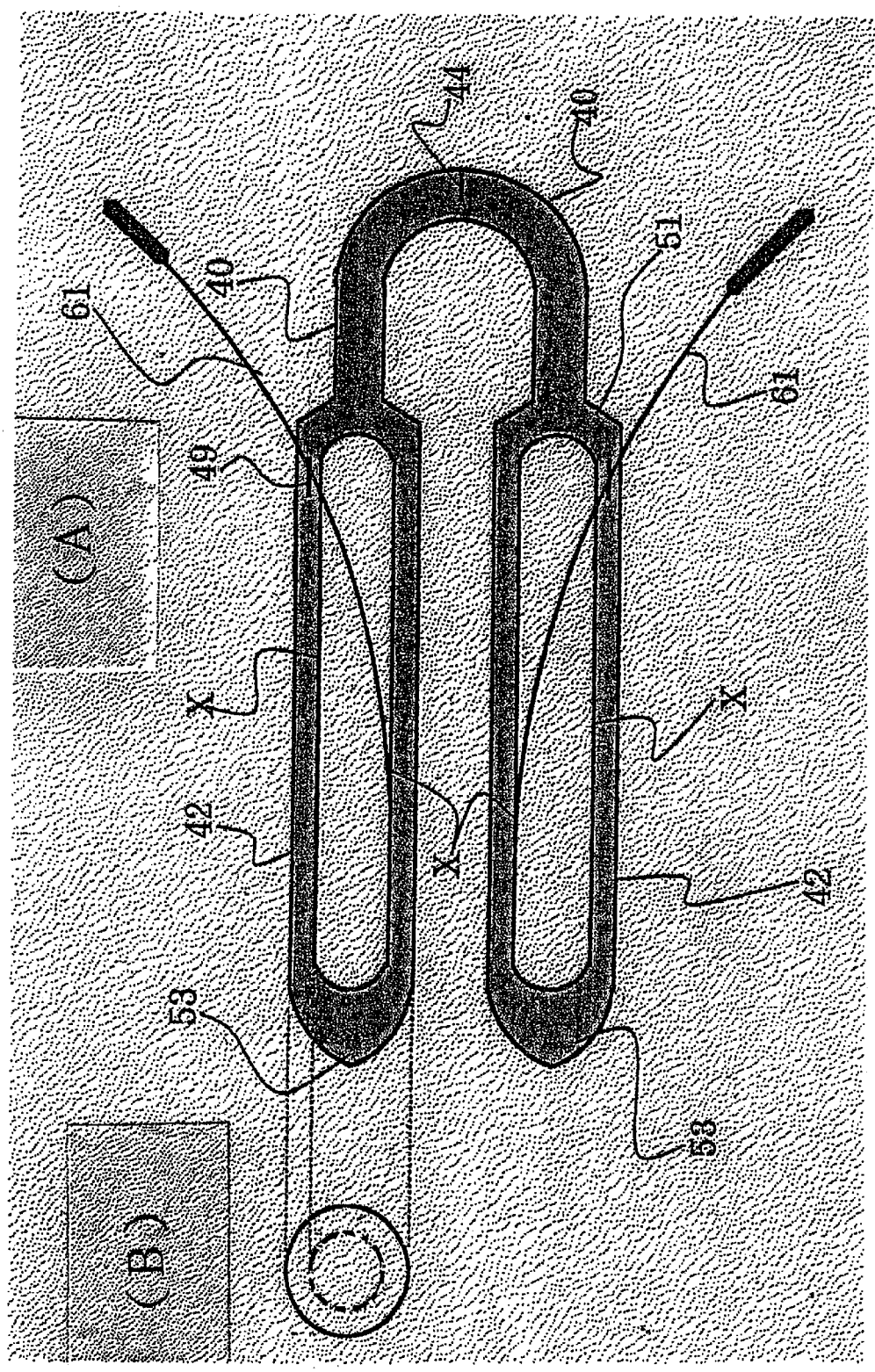
FIG. 3A is a sectional view showing a conventional nunchaku-style tube shown in FIG. 2.
FIG. 3B is an end elevational view showing one end of a conventional nunchaku-style tube shown in FIG. 2.

The apparatus in FIGS. 4~30 can be used as a drug delivery system or in conjunction with a drug delivery system as in the conventional nunchaku-style tube in FIGS. 1~3, and the brim 23 in FIGS. 23~30 can be used as the ocusert which is a drug delivery system for glaucoma, or other drug delivery system (For example see Kurihashi K: Japanese Patent Publication No. 9-276318).

Apparatus for intubation of the lacrimal duct can be easily inserted into the lacrimal duct, resulting in a short operating time and small burden on patients.

What is claimed is:

1. An apparatus for intubation of a lacrimal duct comprising:
    a thinner tube or rod;
    first and second thicker tubes extending from both ends of said thinner tube or rod, each of the thicker tubes defining an inner space and having a small cut;
    a probe insertable through the small cut of one of the thicker tubes to enable the insertion of the thicker tubes and thinner tube or rod into the lacrimal duct, and
    stopping means on an interior surface of at least one of said thicker tubes for stopping a front end of said probe at least at one position intermediate said small cut and a distal end of said one thicker tube.

2. An apparatus for intubation of the lacrimal duct as defined in claim 1, wherein at least the one thicker tube has a shape of a frustum of a circular cone.

3. An apparatus for intubation of the lacrimal duct as defined in claim 1, wherein the inner surface of the thicker tubes has a soft and elastic protuberance(s), groove(s), other irregular surface and/or septum (septa).

4. An apparatus for intubation of the lacrimal duct as defined in claim 1, wherein the thicker tubes consist of two different sized tubes in outer diameter.

5. An apparatus for intubation of the lacrimal duct as defined in claim 1, wherein the thicker tubes are in the shape of carrot.

6. An apparatus for intubation of the lacrimal duct as defined in claim 1, wherein the thicker rod without inner space having a hole is used instead of the thicker tube.

7. An apparatus for intubation of the lacrimal duct as defined in claim 1, wherein a lubricant is applied to the inner part of the thicker tube and/or probe.

8. An apparatus for intubation of the lacrimal duct as defined in claims 1, wherein the boundary portions (51) between the thinner tube (or rod) and thicker tubes (or rods) are positioned in the lacrimal sac—nasolacrimal duct.

9. An apparatus for intubation of the lacrimal duct comprising: the half part of an apparatus defined in claim 1, and a brim wherein the brim is glued with the end of the thinner tube (or rod) and the thinner tube (or rod) is longer than the canalicular length for the boundary portion (51) to be positioned in the lacrimal sac—nasolacrimal duct.

10. An apparatus for intubation of the lacrimal duct defined in claim 1, wherein the thinner tube or rod consists of horizontal, curved and vertical segments.

11. An apparatus for intubation of the lacrimal duct defined in claim 1, wherein the thinner tube or rod consists of a longer segment, a tapered segment, a narrowed segment and a shorter segment.

12. An apparatus for incubation of the lacrimal duct defined in claim 1, wherein the brim is connectable to a drug delivery system.

13. An apparatus for intubation of the lacrimal duct as defined in claim 1, wherein said stopping means comprises at least one protuberance on an inner surface of said one thicker tube.

14. An apparatus for intubation of the lacrimal duct as defined in claim 5, wherein said stopping means further comprises at least one indentation on said inner surface.

15. An apparatus for intubation of the lacrimal duct as defined in claim 1, wherein said stopping means comprises at least one indentation on an inner surface of said one thicker tube.

16. An apparatus for intubation of a lacrimal duct comprising:
    a thinner tube or rod;
    first and second thicker tubes extending from both ends of said thinner tube or rod, each of the thicker tubes defining an inner space and having a small cut;
    a probe insertable through the small cut of one of the thicker tubes to enable the insertion of the thicker tubes and the thinner tube or rod into the lacrimal duct;
    wherein the thicker tubes have inner surfaces which are convex and/or concave in shape; and
    wherein the inner surfaces of the thicker tubes have a step, and the longer the distance from the tip, the larger the diameter of the inner space of each of the thicker tubes becomes.

17. An apparatus for intubation of a lacrimal duct comprising:
    a thinner tube or rod;
    first and second thicker rods extending from both ends of said thinner tube or rod, each of the thicker rods having a small internal duct extending from an opening in a cylindrical surface of the thicker rod toward a tip portion of the thicker rod; and
    a probe insertable through the small duct of one of the thicker rods to enable the insertion of the thicker rods and thinner tube or rod into the lacrimal duct.

* * * * *

UNITED STATES PATENT AND TRADEMARK OFFICE
CERTIFICATE OF CORRECTION

PATENT NO. : 6,383,192 B1 Page 1 of 1
DATED : May 7, 2002
INVENTOR(S) : Katsuaki Kurihashi It is certified that error appears in the above-identified patent and that said Letters Patent is hereby corrected as shown below:

<u>Column 2,</u>
Line 24, "2572340Japanese" should read -- 2572340 Japanese --

<u>Column 8,</u>
Line 14, "incubation" should read -- intubation --

Signed and Sealed this

First Day of October, 2002

*Attest:*

JAMES E. ROGAN
*Attesting Officer*     *Director of the United States Patent and Trademark Office*